United States Patent
D'Agostino et al.

(10) Patent No.: US 9,675,577 B2
(45) Date of Patent: *Jun. 13, 2017

(54) COMPOSITIONS AND METHODS FOR PRODUCING ELEVATED AND SUSTAINED KETOSIS

(71) Applicants: Dominic Paul D'Agostino, Tampa, FL (US); Patrick Arnold, Champaign, IL (US); Shannon Kesl, Tampa, FL (US)

(72) Inventors: Dominic Paul D'Agostino, Tampa, FL (US); Patrick Arnold, Champaign, IL (US); Shannon Kesl, Tampa, FL (US)

(73) Assignee: University of South Florida, Tampa, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/860,092

(22) Filed: Sep. 21, 2015

(65) Prior Publication Data

US 2016/0067207 A1 Mar. 10, 2016

Related U.S. Application Data

(63) Continuation of application No. 14/455,385, filed on Aug. 8, 2014, now Pat. No. 9,138,420, which is a continuation of application No. PCT/US2014/031237, filed on Mar. 19, 2014.

(60) Provisional application No. 61/926,664, filed on Jan. 13, 2014, provisional application No. 61/803,203, filed on Mar. 19, 2013.

(51) Int. Cl.
| | |
|---|---|
| A01N 37/02 | (2006.01) |
| A01N 37/06 | (2006.01) |
| A61K 31/225 | (2006.01) |
| A61K 31/23 | (2006.01) |
| A61K 31/19 | (2006.01) |
| A61K 31/20 | (2006.01) |
| A23L 2/52 | (2006.01) |
| A61K 31/047 | (2006.01) |
| A61K 31/22 | (2006.01) |

(52) U.S. Cl.
CPC ............. *A61K 31/23* (2013.01); *A23L 2/52* (2013.01); *A61K 31/047* (2013.01); *A61K 31/19* (2013.01); *A61K 31/20* (2013.01); *A61K 31/22* (2013.01); *A23V 2002/00* (2013.01)

(58) Field of Classification Search
None
See application file for complete search history.

(56) References Cited

U.S. PATENT DOCUMENTS

| | | |
|---|---|---|
| 5,093,044 A | 3/1992 | Wretlind et al. |
| 5,654,266 A | 8/1997 | Chen et al. |
| 6,207,856 B1 | 3/2001 | Veech |
| 6,316,038 B1 | 11/2001 | Veech |
| 6,323,237 B1 | 11/2001 | Veech |
| 6,613,356 B1 | 9/2003 | Vlahakos |
| 7,351,736 B2 | 4/2008 | Veech |
| 8,101,653 B2 | 1/2012 | Veech |
| 8,124,589 B2 | 2/2012 | Henderson |
| 8,426,468 B2 | 4/2013 | Henderson |
| 2001/0041736 A1 | 11/2001 | Veech |
| 2009/0253781 A1 | 10/2009 | Veech |
| 2010/0041751 A1 | 2/2010 | Henderson |
| 2010/0197758 A1 | 8/2010 | Andrews et al. |
| 2010/0298294 A1 | 11/2010 | Clarke et al. |
| 2012/0071548 A1 | 3/2012 | Veech |

FOREIGN PATENT DOCUMENTS

| | | |
|---|---|---|
| JP | 11060434 | 3/1999 |
| WO | 2005107724 A1 | 11/2005 |
| WO | 2007115282 A2 | 10/2007 |
| WO | WO2008005818 A1 | 1/2008 |
| WO | 2011101171 A1 | 8/2011 |

OTHER PUBLICATIONS

Bastin (Organic Process Research and Development, 2000, 4, 427-435).*
Kirsch, JR et al. "Butanediol Induced Ketosis Increases Tolerance to Hypoxia in the Mouse." Stroke. 1980. vol. 11, No. 5, pp. 506-513.
Kossoff, Eric H. et al. "Optimal Clinical Management of Children Receiving the Ketogenic Diet: Recommendations of the International Ketogenic Diet Study Group." Epilepsia, Feb. 2009;50(2):304-17. Epub Sep. 23, 2008.
Henderson, Samuel T. "Ketone Bodies as a Therapeutic for Alzheimer's Disease." Neurotherapeutics. Jul. 2008;5 (3):470-80.
Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.
Krotkiewski, M. "Value of VLCD Supplementation with Medium Chain Triglycerides." I'nt J Obes Relat Metab Disord. Sep. 2001;25(9):1393-400.

(Continued)

*Primary Examiner* — Dennis Heyer
*Assistant Examiner* — Daniel M Podgorski
(74) *Attorney, Agent, or Firm* — Robert J. Varkonyi; Smith & Hopen, P.A.

(57) ABSTRACT

Beta-hydroxybutyrate mineral salts in combination with medium chain fatty acids or an ester thereof such as medium chain triglycerides were used to induce ketosis, achieving blood ketone levels of (2-7 mmol/L), with or without dietary restriction. The combination results in substantial improvements in metabolic biomarkers related to insulin resistance, diabetes, weight loss, and physical performance in a short period of time. Further, use of these supplements to achieve ketosis yields a significant elevation of blood ketones and reduction of blood glucose levels. Use of these substances does not adversely affect lipid profiles. By initiating rapid ketosis and accelerating the rate of ketoadaptation, this invention is useful for the avoidance of glucose withdrawal symptoms commonly experienced by individuals initiating a ketogenic diet, and minimizes the loss of lean body mass during dietary restriction.

26 Claims, 14 Drawing Sheets

(56) References Cited

OTHER PUBLICATIONS

PCT International Search Report and Written Opinion issued by the International Searching Authority on Jul. 15, 2014 or International Patent Application No. PCT/US2014/031237.
Haywood, A. Glass BD. Pharmaceutical excipient—where do we begin? Australian Prescriber. 2011; 34: 112-114.
First Examination Report issued by the New Zealand Intellectual Property Office on Mar. 10, 2016 for corresponding New Zealand Patent Application No. 711433.
Partial supplementary European search report (EPO Form 1507US) issued by the European Patent Office on Sep. 21, 2016 for corresponding European Application No. 14770025.6.
Search Report and Written Opinion issued by the Intellectual Property Office of Singapore on Apr. 18, 2016 for corresponding Singapore Application No. 11201506780R.
Further Examination Report issued by the New Zealand Intellectual Property Office on Oct. 4, 2016 for corresponding New Zealand Patent Application No. 711433.
First Office Action issued by the Chinese State Intellectual Property Office on Nov. 4, 2016 for corresponding Chinese Patent Application No. 201480016818.0.
English Translation of First Office Action issued by the Chinese State Intellectual Property Office on Nov. 4, 2016 or corresponding Chinese Patent Application No. 201480016818.0.
Written Opinion issued by the Intellectual Property Office of Singapore on Dec. 28, 2016 for corresponding Singapore Patent Application No. 11201506780R.
Extended European Search Report pursuant to Rule 62 EPC (EPO Form 1507S) issued on Jan. 24, 2017 for corresponding European Patent Application No. 14770025.6.
Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.
Vogerd, M. And J. Zange. Treatment of glycogenosys type V (McArdle disease) with creatine and ketogenic diet with clinical scores and with 31P-MRS on working leg muscle. Acta Myologica, 2007; XXVI; pp. 61-63.

\* cited by examiner

COMPOSITIONS AND METHODS FOR PRODUCING ELEVATED AND SUSTAINED KETOSIS

CROSS-REFERENCE TO RELATED APPLICATIONS

This application is a continuation of and claims priority to U.S. application Ser. No. 14/455,385, entitled: "Compositions and Methods for Producing Elevated and Sustained Ketosis," filed on Aug. 8, 2014, which is a continuation of and claims priority to International Patent Application No. PCT/US2014/031237, filed Mar. 19, 2014 which claims priority to U.S. Provisional Patent Application No. 61/803,203, entitled: "Compositions and Methods for Producing Elevated and Sustained Ketosis," filed on Mar. 19, 2013, and U.S. Provisional Pat. Application No. 61/926,664, entitled: "Methods of Sustaining Dietary Ketosis and Its Effects on Lipid Profile," filed Jan. 13, 2014, the contents of which are herein incorporated by reference.

STATEMENT OF GOVERNMENT SUPPORT

This invention was made with government support under Grant #N00014-13-1-0062 awarded by the Department of Defense, Office of Naval Research. The government has certain rights in the invention.

FIELD OF THE INVENTION

This invention relates to the use of ketogenic precursors to quickly produce elevated and sustained levels of ketone bodies in the blood and methods for assisting the body's transition into nutritional ketosis. Specifically, the use of a combination of medium chain triglycerides (MCT) with mineral salts of beta-hydroxybutyrate (βHB) is presented to provide an easy and accelerated method for inducing and sustaining nutritional ketosis.

BACKGROUND OF THE INVENTION

Nutritional, or therapeutic, ketosis is the physiological state of elevated blood ketone body levels (typically above 0.5 mmol/L) resulting from ketogenic diets, calorie restriction, therapeutic fasting and/or supplementation with ketogenic precursors. Ketone bodies represent alternative energy substrates for both peripheral tissues and the central nervous system. The two most abundant and physiologically significant ketone bodies are acetoacetate and β-hydroxybutyrate (βHB), while the third ketone body, acetone, is produced as a byproduct that the lungs breathe off. The body produces ketone bodies during nutritional or therapeutic ketosis in the range of 2-16 mmol/L. The metabolism of ketone bodies is associated with anticonvulsant effects, enhanced brain metabolism, neuroprotective, muscle sparing properties and improvement in cognitive and physical performance. Science-based improvements in efficiency of cellular metabolism, managed through ketone supplementation, could have beneficial impacts on physical, cognitive health, psychological health, warfighter resilience and a long-term impact on health with respect to the common avoidable diseases such as obesity, neurodegenerative diseases, diabetes and cancer.

Under normal conditions of the standard American diet, the brain is exclusively dependent upon the metabolism of glucose to supply its metabolic energy. Though the brain is only 2% of bodyweight, it represents 25% of total glucose consumption. Ketones can replace glucose to supply most of the brain's metabolic energy needs (>50%) during periods of limited glucose availability resulting from starvation/fasting, caloric restriction or carbohydrate restriction as in ketogenic diets. During carbohydrate deprivation, glucose availability decreases causing a metabolic shift towards fatty acid beta-oxidation and the production of ketone bodies for energy homeostasis.

Dietary carbohydrates (carbs) include simple sugars, such as table sugar (sucrose) and complex carbohydrates (starch) found in foods like potatoes and pasta. Carbohydrate and sugar consumption have dramatically increased in the last two centuries in Western societies. When sugars and carbohydrates are consumed by humans, the pancreas secretes insulin, a hormone used to convert the sugars and carbohydrates into glucose. The glucose is then used by the body as a fuel source. In most Western diets, glucose is the body's primary fuel source.

In periods of fasting, extreme exercise, and/or low carbohydrate consumption, glucose stores in the body are rapidly used and can become quickly depleted. Failure to replenish glucose stores as they become depleted causes the body to turn to an alternative method to generate energy by creating ketone bodies. Ketone bodies can be used by every cell of the body as a replacement fuel to satisfy the body's energy needs, including the needs of the brain. During a prolonged fast, for example, blood ketone levels will increase to as high as 2 or 3 mmol/L. It is conventionally understood and agreed that when blood ketones rise above 0.5 mmol/L, the heart, brain and peripheral tissues are using ketone bodies (beta hydroxybutyrate and acetoacetate) as the primary fuel source. This condition is referred to as ketosis, or "nutritional ketosis." This is distinguished from, and should not be confused with, diabetic or alcoholic ketoacidosis, which is the runaway accumulation of ketone bodies and associated drop in blood pH. Diabetic ketoacidosis is associated with the absence of insulin as occurs in those suffering from type 1 diabetes. Ketoacidosis typically results in blood ketone levels in excess of 25 mmol/L in combination with metabolic derangement and electrolyte imbalance.

When in ketosis, the body essentially burns fat for fuel. This is accomplished because fat stores in the body are utilized to create the water soluble ketone bodies beta-hydroxybutyrate (βHB) and acetoacetate (also known as acetylacetonate). These ketone bodies are then used by the body as its primary energy source.

The body enters a state of ketosis when it has no dietary source of glucose or sugar and its stores of glycogen have been depleted. This typically occurs during fasting, exercise, and/or pursuing a carbohydrate restricted ketogenic diet. Upon transitioning into ketosis, the body begins cleaving fats into fatty acids and glycerol and transforms the fatty acids into acetyl CoA molecules which are then eventually transformed into ketone bodies in the liver. In other words, during ketogenic metabolism in the liver, the body uses dietary and bodily fats as its primary energy source. Consequently, once in ketosis, one can easily induce loss of body fat by reducing dietary fat intake and adjusting carbohydrate intake low enough to sustain ketosis.

Effects of Ketosis on Cognitive and Physical Performance

Performance studies in rats, mice and human subjects have shown improved motor function, endurance and cognitive function with ketone supplementation. Resilience of cardiopulmonary and neurological function under extreme environments of oxidative stress (hyperoxia) has been achieved in rats given ketone supplementation Many people on a ketogenic diet report greater mental clarity, an enhanced ability to multi-task, and a more favorable and balanced mood.

Other advantages to the ketogenic diet including anti-aging and mood stabilizing effects. Recent animal studies have demonstrated superior performance with respect to endurance time, volume of oxygen consumed, heart rate, blood lactate levels and power output when blood ketone levels are elevated.

Therapeutic Ketosis to Ameliorate Disease

The ketogenic diet has been established to be efficacious in treating drug-resistant seizure disorders. This therapeutic method is well established in children and adults. The ketogenic diet has been used to treat pediatric intractable seizures since the 1920s. The diet is currently being investigated as treatment for a broad list of disease states from cardiovascular health and type II diabetes to cancer and neurological disorders such as amyotrophic lateral sclerosis (ALS) and traumatic brain injury. The metabolic adaptations associated with a ketogenic diet improve mitochondrial function, decrease reactive oxygen species (ROS) production, reduce inflammation and increase the activity of neurotrophic factors. Thus, using ketones to treat traumatic brain injury has also been suggested. Additionally, some studies have suggested that certain cancer cells cannot live on ketones and therefore investigation of therapeutic ketosis for cancer is underway.

As disclosed in studies relating to the effects of ketosis on cognition and performance, medium chain triglyceride diets have been used to alleviate symptoms of Alzheimer's disease and dementias, as seen in Henderson, et al. (U.S. Pat. No. 8,426,468). As Alzheimer's disease was attributed to decreased neuronal metabolism and reduced glucose availability to neurons, it was suggested that elevating ketone bodies in these patients provides an alternative fuel source for the neurons. Lipases hydrolyze the medium chain triglycerides to medium chain fatty acids in the duodenum, permitting uptake of the medium chain fatty acids that are subsequently oxidized by the liver to form ketone bodies. Alternatively, Henderson, et al. suggested intravenous administration of medium chain triglycerides, medium chain fatty acids, or ketone bodies. The increase in blood ketone levels provides neurons with a supplemental fuel where glucose is not accessible to the neuron, such as in Alzheimer's disease. Henderson (U.S. Pat. No. 8,124,589) used oral compositions of medium chain triglycerides to treat age-associated memory impairment, thereby increasing ketone body levels in the blood. Veech (U.S. Pat. No. 6,323,237) also disclosed compositions containing ketone bodies for treating neuronal damage, and also found the compositions useful for increasing cardiac efficiency, providing energy to diabetics and patients suffering from insulin resistance. The compositions include esters and polymers. As amyloid proteins responsible for Alzheimer's disease block pyruvate dehydrogenase, which is part of glucose metabolism, ketone bodies such as D-β-3-hydroxybutarate, acetoacetate, and derivatives of these compounds are useful fuel sources.

Ketogenic Diets and Weight Loss

A ketogenic diet is one that is high in dietary fat and low in carbohydrates with moderate levels of protein (approximately 1-2 g/kg). The classical ketogenic diet consists of a strict regimen of 4 parts fat to 1 part protein with less than 25-50 g of carbohydrates per day. It has been suggested that the ideal macronutrient ratio to maintain a ketogenic diet is 65-85 percent of calories from fats, 10-20 percent of calories from proteins, and 5 percent of calories from carbohydrates.

A significant advantage of pursuing weight loss through a ketogenic diet is that a ketogenic diet may result in loss of fat stores while maintaining and protecting muscle mass. Some studies have suggested that the muscle sparing properties of a ketogenic diet result in improvement in physical performance. Athletes who maintain nutritional ketosis maintain lower insulin levels and can better utilize fatty acids and ketones for fuel, effectively sparing blood glucose, which optimizes and prolongs physical and mental performance. This state is referred to as being "keto adapted." Keto adaptation occurs when the body adjusts to ketosis by building up the necessary fat-burning enzymes, hormone levels are changed to accommodate ketosis, glycogen stored in muscles and liver is reduced, and the body is carrying less water.

Individuals on the standard American diet can expect to get peak fat oxidation while exercising from between 60 to 65 percent of their maximum oxygen consumption ($VO_2$ max); higher exertion levels will then deplete glycogen stores. Keto-adapted individuals draw proportionally more substrate from fats and ketones (sparing glycogen) and can shift the peak to much higher $VO_2$ levels and thus sustain effort for an extended duration. Transitioning to a keto-adapted state (blood ketones >0.5 mmol/L) typically requires 1 to 2 weeks with severe restriction of carbohydrates (<25 g/day) and moderate protein restriction (1 g/kg/day) with the balance of macronutrient from fat. A sustained physiological decrease in glucose and insulin are required for sustained hepatic ketogenesis, which is very difficult for most humans.

Vlahakos (U.S. Pat. No. 6,613,356) provides a weight-loss composition using n-butyrate ions from potassium butyrate or related compounds. Butyric acid stimulates receptors in the stomach that the stomach is full and food is stagnant in the stomach. Thus, consuming butyric acid precursors prior to eating reduces food consumption. Testing showed the compositions improved a patient's ability to withstand rigorous exercise, improved hypercholesterolemia and hypertriglyceridemia, and reduced fatigue.

Another advantage to pursuing weight loss through a ketogenic diet is that being in ketosis reduces hunger. Indeed, hunger is the major barrier that is often cited for the inability to maintain a traditional calorie restricted diet.

Despite the many health advantages to pursuing a ketogenic diet and maintaining a state of nutritional ketosis, there remain significant barriers to pursuing and maintaining a ketogenic lifestyle. One of these barriers is the difficulty of transitioning into a ketogenic state. The fastest way to deplete glucose stores in the body is through fasting combined with exercise. This is physically and emotionally demanding and is an extreme challenge even for the most motivated and disciplined.

Individual reports recounting the difficulties of entering ketosis when using a dietary approach have been widely published. In a typical example, an individual reported no effects on blood ketone levels even after four days of strict adherence to a ketogenic diet (80% fat/20% protein; 90% of maintenance calories; less than 15 grams of carbs in any given day). Another common experience is extreme hunger during a weeklong ketogenic diet without experiencing satiety during meals unless 100-200 g of carbohydrates per day were consumed.

The ability for much larger numbers of people to utilize the significant advantages of ketosis are severely restricted by the ability to get into ketosis. This invention opens up the potential for large numbers of people to quickly and easily get into ketosis and be able to sustain a ketogenic lifestyle without the physiological and emotional challenges brought on through the process of getting into and sustaining ketosis.

Additionally, the transition into ketosis causes lethargy and light-headedness in many, resulting in an uncomfortable physiological and mental state commonly referred to as the "low carb flu." Some suggest that these transitory symptoms may last as long as two to three weeks. If any carbohydrates over the restrictive amount are consumed, there is an immediate shift back to glucose utilization and the transition into ketosis must begin anew.

The symptoms associated with transitioning from a sugar and carbohydrate-rich diet into a state of ketosis will vary according to the physiology of the particular subject. Thus, some people may experience minimal discomfort as they transition into ketosis. On the other hand, however, some people may experience these symptoms to such a degree that the symptoms present what may seem to be an insurmountable impediment to getting into ketosis and taking advantage of the positive health effects that can be achieved by living in a state of ketosis. The vast majority of those who attempt to induce ketosis through some combination of diet, fasting, and exercise will experience some of these symptoms.

Because the presence of blood ketones can be easily measured by a urine test using one of many ketone test strips available on the commercial market, those desirous of pursuing a state of ketosis can easily measure their progress. Just as those on a traditional diet can weigh themselves and gain positive feedback by measuring weight loss, those pursuing a state of ketosis can also be encouraged by measuring their blood ketone levels. However, when transitioning into ketosis, it may take from several days to two weeks or longer for any measurable increase in blood ketone levels to manifest through a urine test. This lack of measurable progress can be yet another impediment to pursuing a state of ketosis.

Following a ketogenic diet requires eliminating substantially all sugars and carbohydrates from the diet. To someone who derives pleasure from eating cakes, candies, breads, and other non-ketogenic foods, the necessary modification to their diet will pose an additional hurdle to pursuing nutritional ketosis. With proper education and advance planning, implementing a ketogenic meal plan at home is manageable for many. However, because restaurant dining is part of the social fabric for many people, maintaining a ketogenic diet in such social settings requires further education and may place one in awkward social settings, providing yet another impediment to widespread implementation of a ketogenic diet. Additionally, in today's society, many people frequently travel. For a frequent traveler to maintain a ketogenic diet will typically require that they either carry appropriate food with them or attempt to maintain the ketogenic diet in settings where few, if any, ketogenic foods may be available.

It has been suggested that transitioning into ketosis may be aided by taking ketogenic medical foods or exogenous supplemental ketones. However, ketogenic fats like medium chain triglyceride oil (MCT oil) are generally not well tolerated by the gastrointestinal system in quantities necessary to aid in inducing ketosis. Additionally, oral administration of βHB and acetoacetate in their free acid form is expensive and ineffective at producing sustained ketosis. One idea has been to buffer the free acid form of βHB with sodium salts, but this causes a potentially harmful sodium overload and mineral imbalance at therapeutic levels of ketosis and is largely ineffective at preventing seizures in animal models. Ketone salts with a balance of minerals are needed to prevent the sodium overload, but these ketone mineral salts have not been developed or commercialized yet.

Concerns have been raised about ketogenic diets increasing total cholesterol and triglycerides while decreasing high density lipoprotein (HDL) levels. This lipid profile is a key predictor of heart health: atherosclerotic lesions, fatty streaks and fibrous plaques in the aorta and coronary arteries. This is more limiting during adult treatment with the ketogenic diet. Based on the broad therapeutic potential for pursuing and sustaining a ketogenic lifestyle, the need to develop an oral ketone supplement that could safely elevate blood ketone levels to therapeutic ranges of nutritional ketosis without severe dietary restriction and the associated side effects is greater than ever.

As such, what is needed is a composition and corresponding treatment and maintenance method that permits the establishment of ketosis in a patient quickly, and the maintenance of ketosis with little to no perceived impact on the patient's physiology or mental comfort.

SUMMARY OF THE INVENTION

A ketogenic diet is effective at raising blood ketone levels and has potential broad applications, but achieving the advantages of those applications requires strict compliance with the diet. The present invention provides a strategy to elevate and sustain blood ketone body levels through the administration of novel combinations of ketogenic supplements and causes a rapid and sustained elevation of blood ketones with a single oral administration. The invention exploits the metabolic and physiological advantages of sustained ketosis (e.g. keto-adaptation) which utilizes ketones as an alternative fuel to improve metabolic health, physical performance and enhance disease prevention.

As such, a composition of ketone precursors is disclosed which comprises at least one medium chain fatty acid, or an ester thereof such as a medium chain triglyceride, and a β-hydroxybutyrate ketone source or precursor. There are numerous sources of ketones and ketogenic precursors. Nonlimiting examples of the beta-hydroxybutyrate compound include beta-hydroxybutyrate salts such as sodium beta-hydroxybutyrate and arginine beta-hydroxybutyrate, potassium beta-hydroxybutyrate, calcium beta-hydroxybutyrate, magnesium beta-hydroxybutyrate, lithium beta-hydroxybutyrate, lysine beta-hydroxybutyrate, histidine beta-hydroxybutyrate, ornithine beta-hydroxybutyrate, creatine beta-hydroxybutyrate, agmatine beta-hydroxybutyrate, citrulline beta-hydroxybutyrate, beta-hydroxy butyrate sodium salt, beta-hydroxy butyrate potassium salt, beta-hydroxy butyrate calcium salt, beta-hydroxy butyrate magnesium salt, or a combination of salts. Nonlimiting examples of combinations of beta-hydroxybutyrate salts include sodium beta-hydroxybutyrate and arginine beta-hydroxybutyrate, or beta-hydroxy butyrate sodium salt and beta-hydroxy butyrate potassium salt. Other β-hydroxybutyrate ketone sources include, without limiting the scope, 1,3-butanediol, ethyl acetoacetate, and ethyl beta-hydroxybutyrate. The compounds, are optionally administered between 2 grams and 50 grams, between 5 grams and 30 grams, or between 10 grams and 20 grams. For example, the ketone compounds are optionally administered at 2 grams, 4 grams, 5 grams, 6 grams, 7 grams, 8 grams, 9 grams, 10 grams, 11 grams, 12 grams, 13 grams, 14 grams, 15 grams, 17 grams, 19 grams, 20 grams, 22 grams, 24 grams, 26 grams, 28 grams, 30 grams, 32 grams, 34 grams, 36 grams, 38 grams, 40 grams, 42 grams, 44 grams, 46 grams, 48 grams, or 50 grams.

In some variations of the invention, the beta-hydroxybutyrate compound is histidine beta-hydroxybutyrate, ornithine beta-hydroxybutyrate, creatine beta-hydroxybutyrate, agmatine beta-hydroxybutyrate, or citrulline beta-hydroxybutyrate. The compound is optionally a racemic DL-beta hydroxybutyrate or the single isomer R-beta hydroxybutyrate.

It is also contemplated that additional ketone precursors or supplements might be used in combination with beta hydroxybutyrate and medium chain triglycerides. These additional ketone precursors or supplements might include acetoacetate, ketone esters, and other compounds that cause a rise in blood ketone levels.

As noted, many individuals, especially females, experience lethargy and light-headedness, referred to by some as the "low carb flu," caused by glucose withdraw in the brain and to a depletion of minerals, especially sodium and potassium in the plasma when entering ketosis through a ketogenic diet. These symptoms can be attenuated or reversed with sufficient supplementation of sodium, potassium, calcium and magnesium. Supplemental administration of minerals prevents potassium depletion via the renal-adrenal aldosterone pathway. As such, the invention optionally uses mineral salts of beta-hydroxybutyrate (βHB). Mineral salts of βHB are described above and include, without limiting the scope of the invention, potassium βHB, sodium βHB, calcium βHB, magnesium βHB, lithium βHB and any other feasible non-toxic mineral salts of βHB. Organic salts of βHB include, without limiting the scope of the invention, salts of organic bases such as arginine βHB, lysine βHB, histidine βHB, ornithine βHB, creatine βHB, agmatine βHB, and citrulline βHB. The salts may contain the racemic DL-beta hydroxybutyrate or the single isomer R-beta hydroxybutyrate.

Non-limiting examples and sources of the medium chain fatty acid, or an ester thereof such as a medium chain triglyceride, include coconut oil, coconut milk powder, fractionated coconut oil, palm oil, palm kernel oil, caprilic acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc. Oils may be spray dried onto solid supports such as maltodextrin to facilitate delivery in powder form. The at least one medium chain triglyceride is optionally administered at between 5 grams and 50 grams, between 10 grams and 40 grams, or between 15 grams and 30 grams. As a nonlimiting example, the medium chain triglyceride is administered at 5 grams, 6 grams, 7 grams, 8 grams, 9 grams, 10 grams, 11 grams, 12 grams, 13 grams, 14 grams, 15 grams, 17 grams, 19 grams, 20 grams, 22 grams, 24 grams, 26 grams, 28 grams, 30 grams, 32 grams, 34 grams, 36 grams, 38 grams 40 grams.

The composition optionally includes at least one non-toxic mineral salt. Nonlimiting examples include the minerals Na, Mg, V, K, Cr, Mn, Co, Cu, Zn, As, Mo and Se associated with an ion of chlorine, sulfate, iodine, bromine, or other known ion in the art. Examples include sodium chloride, zinc sulfide, potassium iodine.

The ketone precursors are preferably ingested along with nutritional substrates such as free amino acids, amino acid metabolites, vitamins, minerals, electrolytes and metabolic optimizers such as NADH, soluble ubiquinol, tetrahydrobiopeterin, alpha-ketoglutaric acid, carnitine, and/or alpha lipoic acid, nutritional co-factors, calcium beta-methyl-beta-hydroxybutyrate, arginine alpha-ketoglutarate, sodium R-alpha lipoic acid, thiamine, riboflavin, niacin, pyridoxine, ascorbic acid, citric acid, malic acid, sodium benzoate, potassium sorbate, acesulfame K, aspartame, xanthan gum, or a combination thereof. Nonlimiting examples of nutritional co-factors include R-alpha lipoic acid, acetyl-1-carnitine, ketoisocaproate, alpha-ketoglutarate, alpha-hydroxyisocaproate, creatine, branched chain amino acids (leucine, isoleucine, valine), beta-hydroxy-beta methylbutyrate (HMB), B vitamins, vitamin C, soluble ubiquinol, and carnitine that assist in mitochondrial function. In some variations, the supplemental mixture shall provide no more than 400 calories per day.

The compositions are useful for weight loss and treatment of high blood glucose or type II diabetes and can improve the user's general health in a short period of time. In another embodiment, the βHB salt/medium chain triglyceride formula is used to facilitate weight loss, as a brain tonic, to enhance athletic performance, to help prevent diseases related to metabolic dysfunction, mitochondrial defect, and insulin resistance, as an adjunct to a ketogenic diet, as an anti-aging supplement, and other uses associated with improved metabolic health. A combination βHB/MCT composition is optionally administered in a range of 1:1 to 1:2 mixture to elevate blood ketones to a level that would be considered a state of nutritional ketosis. Administration can be performed with or without dietary restriction. In some variations, the patient preferably follows a ketogenic diet that restricts intake of carbohydrates and protein during the period of administration of the βHB/MCT composition. In specific embodiments, the patient restricts the dietary intake to a ratio of about 65% fat, 25% protein, and 10% carbohydrates. The therapeutic ketosis produced herein provides a rapid and sustained keto-adaptation as a metabolic therapy for a wide range of metabolic disorders, and provides nutritional support for therapeutic fasting, weight loss, and performance enhancement. As such, the composition is optionally administered once per day, twice per day, or three times per day to a subject desiring to promote and/or sustain a state of ketosis.

In an embodiment of the invention, the preferred route of administration of the mixture of βHB salts and MCT oil is oral. The product may be delivered as a powdered mixture, as a ready-to-drink liquid, in hard or soft gelatin caps, as hard-pressed tablets, concentrated gels, or any other dosage form known to those trained in the art. The product is preferably delivered in the form of a ready-to-drink formula consisting of a mixture of sodium and potassium βHB along with coconut milk powder. The drink may be pH adjusted with citric and/or malic acid, and artificial sweetener and flavoring can be added. The drink should be homogenized and pasteurized.

Because the supplements and methods of the present invention will raise the level of blood ketones, the subject may enjoy greater flexibility in the diet that must be followed to maintain a state of ketosis. Thus, while consistently taking the supplement of the present invention, a subject may be able to enjoy an occasional carbohydrate or sugar "cheat" and not significantly jeopardize their ketogenic state. Indeed, because the present invention facilitates the quick and easy transition into ketosis, should one need to depart from a strict ketogenic diet for a day or two, getting back into ketosis can be accomplished quickly and without the difficult symptoms which heretofore impeded the process.

Through the consumption of the supplements of the present invention, a measurable increase in blood ketones can often be observed within hours of taking the supplements. This is particularly true if the subject maintains a ketogenic diet while taking the supplements. Thus, whereas it may take weeks to measure an increase of blood ketones following a ketogenic diet alone, the utilization of the present invention will allow the increase of blood ketones to be measured quickly, thereby encouraging and motivating those pursuing a state of ketosis.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
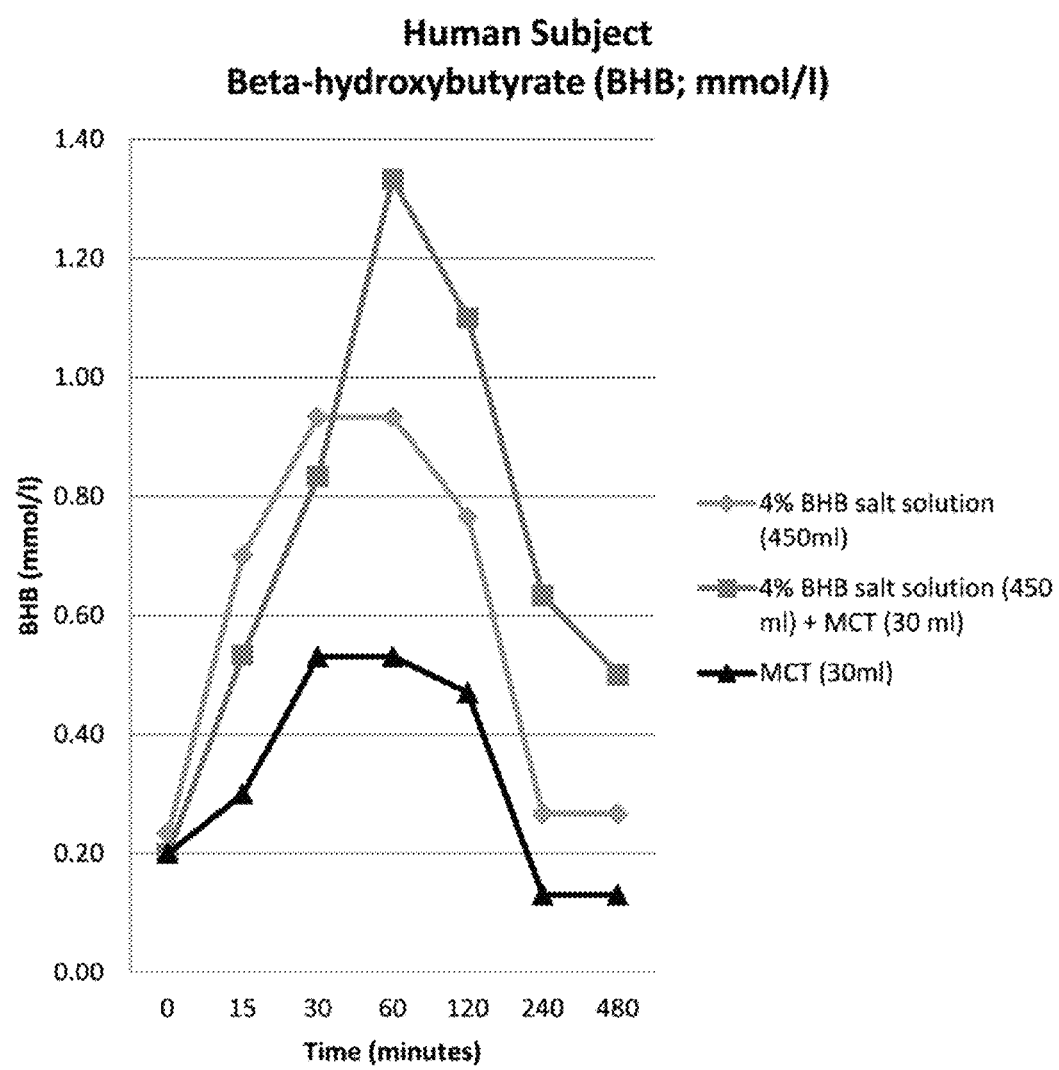
FIG. 1 is a graph depicting summary data of mean blood βHB levels of a human subject that received βHB salts (4% solution containing 11 grams sodium βHB and 7.1 grams potassium βHB), MCT oil, or the combination of βHB salts and MCT oil, at 15, 30, 60, 120, 240 and 480 minutes after oral administration.

In the following detailed description of preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used herein "beta-hydroxybutyrate," also known as βHB or BHB, is a carboxylic acid having the general formula $CH_3CH_2OHCH_2COOH$ which may be utilized by a patient's body as a fuel source during instances of low glucose levels in the patient and is considered a ketone body. In the present invention, salt variants of beta-hydroxybutyrate are disclosed.

As used herein "patient", means members of the animal kingdom, including mammals, such as but not limited to, primates including humans, gorillas and monkeys; rodents, such as mice, fish, reptiles and birds. The patient may be any animal requiring therapy, treatment, or prophylaxis, or any animal suspected of requiring therapy, treatment, or prophylaxis. The term treatment, as used in this definition only, is intended to mean that regiment described is continued until the underlying disease is resolved, whereas therapy requires that the regiment alleviate one or more symptoms of the underlying disease. Prophylaxis means that regiment is undertaken to prevent a possible occurrence, such as where a high glucose or diabetes is identified. "Patient" and "subject" are used interchangeably herein.

"Ketosis" as used herein refers to a subject having blood ketone levels within the range of about 0.5 mmol/L and about 16 mmol/L in a subject. Ketosis may improve mitochondrial function, decrease reactive oxygen species production, reduce inflammation and increase the activity of neurotrophic factors.

"Keto-adaptation" as used herein refers to prolonged nutritional ketosis (>1 week) to achieve a sustained non-pathological "mild ketosis" or "therapeutic ketosis."

The term "medium chain triglycerides" (MCT) are molecules having a glycerol backbone attached to three medium chain fatty acids. Medium chain fatty acids range from 6 to 12 carbon atoms in length. Exemplary fatty acids are caprylic acid, also known as octanoic acid, comprising 8 carbon molecules, and capric acid, also known as decanoic acid, comprising 10 carbon molecules.

The term "administration" or "administering" is used to describe the process in which individual ketone esters or beta-hydroxybutyrate salts in any combination with medium chain fatty acid derivatives are delivered to a subject. The composition may be administered in various ways including oral, intragastric, and parenteral (referring to intravenous and intra-arterial and other appropriate parenteral routes), among others. Each of these conditions may be readily treated using other administration routes of beta-hydroxybutyrate salts in combination with medium chain triglycerides, derivatives, or any combination thereof to treat a disease or condition.

Administration will often depend upon the amount of compound administered, the number of doses, and duration of treatment. In an embodiment, multiple doses of the agent are administered. The frequency of administration of the agent can vary depending on any of a variety of factors, such as timing of treatment from previous treatments, objectives of the treatment, i.e., weight loss or treatment of cancer or neurological disease, and the like. The duration of administration of the agent, e.g., the period of time over which the agent is administered, can vary, depending on any of a variety of factors, including patient response, desired effect of treatment, etc.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art.

The "therapeutically effective amount" for purposes herein is thus determined by such considerations as are known in the art. A therapeutically effective amount of individual beta-hydroxybutyrate salts in combination with medium chain triglycerides, derivatives, or any combination thereof is that amount necessary to provide a therapeutically effective result in vivo. The amount of beta-hydroxybutyrate salts in combination with medium chain triglycerides, derivatives, or any combination of beta-hydroxybutyrate salts in combination with medium chain triglycerides or derivatives thereof must be effective to achieve a response, i.e. therapeutic ketosis. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

The amount of the beta-hydroxybutyrate salts in combination with medium chain triglycerides or derivatives will depend on absorption, distribution, metabolism, and excretion rates of the beta-hydroxybutyrate salts in combination with medium chain triglycerides or derivatives, the particular beta-hydroxybutyrate salts in combination with medium chain triglycerides or derivatives, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

Statistics

All data are presented as the mean±standard error of the mean (SEM). All calculations were performed using statistical analysis software GraphPad PRSIM™ version 6.0a. Statistical significance was defined as $p<0.05$. All data were compared to control at the applicable time points using a two-way ANOVA with Dunnet's multiple comparisons test.

The invention presented herein details the unexpected benefit of the combination of medium chain triglycerides with βHB salts for the sustained elevation of ketone bodies when taken orally by mammals. The combination of βHB salts with medium chain triglycerides disclosed herein produced blood ketone levels at a rate and peak level greater than what was achieved with either component alone. Unexpectedly, in later time periods, this elevation in blood ketones is sustained at a higher level than what would be anticipated based on the sum of data from the ingestion of each component separately. The combination of medium chain triglycerides with βHB salts allows for lower dosing of the components as compared to administering the individual compounds, thereby reducing side effects and resulting in a novel blood ketone profile.

Fasting can have many health benefits; however, it is often accompanied by discomfort due to hunger and lack of energy substrate (glucose) for proper brain function and depletion of sodium and potassium. Additionally it can be associated with deleterious loss of lean body mass. This invention reduces hunger, supplies an alternative energy substrate to the brain (ketones) and confers a protein sparing effect that preserves skeletal muscle mass. The following examples provide evidence for the use of supplemental ketones to elevate and sustain blood levels of βHB while maintaining low and controlled blood glucose.

Example 1—A 100 kg Male Subject

All procedures were done in accordance with the University of South Florida Institutional Review Board (IRB) guidelines. BHB salts and MCT oil were given to human subjects as a ketogenic food supplement and blood measurements of BHB and/or glucose were taken at predetermined time points.

To determine the time course of ketosis, the subjects were orally given the test substances of a BHB salt solution (450 mL; 4%, approximately 18 g), an MCT oil (30 mL, approximately 30 g), or a combination of the BHB salt solution and an MCT oil. Blood concentrations of glucose and BHB were determined utilizing a commercially available glucose/ketone monitoring system (Precision Xtra® blood glucose and ketone meter) at defined time points (0, 15, 30, 60, 120, 240 and 480 minutes following ingestion of the test substances).

The subject was administered a βHB salt solution containing 4% $Na^+/K^+$ BHB salts in solution, an MCT oil, or a combination of the 4% $Na^+/K^+$ BHB salts and the MCT oil. At 15, 30, 60, 120, 240 and 480 minutes after administration, blood was drawn. The subject returned on days 2 and 3 for additional supplements, with blood taken as on day 1. Levels of BHB in the blood were determined as described above. Administration of the $Na^+/K^+$ BHB salt solution showed that plasma levels of BHB peaked at 30 to 60 minutes after administration, as seen in Table 1 and FIG. 1.

TABLE 1

Blood βHB levels (mmol/L) of a 100 kg male subject following a single daily of oral administration of either βHB salts (4% solution containing 11 grams sodium βHB and 7.1 grams potassium βHB), 30 mL of MCT oil or 11.1 g of βHB salts + 20 mL of MCT oil at 15, 30, 60, 120, 240 and 480 minutes on three consecutive days.

| Supplementation | Time Min | Day 1 mM | Day 2 mM | Day 3 mM | Mean mM |
|---|---|---|---|---|---|
| BHB salt (450 mL) | 0 | 0.2 | 0.4 | 0.1 | 0.23 |
|  | 15 | 0.5 | 0.8 | 0.8 | 0.70 |
|  | 30 | 0.8 | 0.8 | 1.2 | 0.93 |
|  | 60 | 1 | 0.6 | 1.2 | 0.93 |
|  | 120 | 1.2 | 0.3 | 0.8 | 0.77 |
|  | 240 | 0.4 | 0.1 | 0.3 | 0.27 |
|  | 480 | 0.3 | 0.2 | 0.3 | 0.27 |
| MCT (30 mL) | 0 | 0.1 | 0.3 | 0.2 | 0.20 |
|  | 15 | 0.2 | 0.3 | 0.4 | 0.30 |
|  | 30 | 0.4 | 0.8 | 0.4 | 0.53 |
|  | 60 | 0.5 | 0.6 | 0.5 | 0.53 |
|  | 120 | 0.5 | 0.6 | 0.3 | 0.47 |
|  | 240 | 0.1 | 0.2 | 0.1 | 0.13 |
|  | 480 | 0.2 | 0.1 | 0.1 | 0.13 |
| BHB salt (450 mL) + MCT (30 mL) | 0 | 0.1 | 0.3 | 0.2 | 0.20 |
|  | 15 | 0.5 | 0.7 | 0.4 | 0.53 |
|  | 30 | 0.7 | 0.8 | 1.0 | 0.83 |
|  | 60 | 1.3 | 1.2 | 1.5 | 1.33 |
|  | 120 | 0.9 | 1.2 | 1.2 | 1.10 |
|  | 240 | 0.4 | 1.0 | 0.5 | 0.63 |
|  | 480 | 0.4 | 0.8 | 0.3 | 0.50 |

Administration of MCT oil showed little elevation in BHB levels. Administration of BHB salts showed higher elevation in BHB levels than MCT oil alone. The combination of BHB salts showed further elevation in BHB levels than either BHB salts or MCT oils alone. In comparison, administration of $Na^+/K^+$ BHB salt solution or the MCT oil alone showed peak BHB levels at 60 minutes, which remained fairly elevated through 120 minutes after administration, as seen in Tables 1 and 2 and FIG. 1. Further, administration the combination of $Na^+/K^+$ BHB salt solution and MCT oil increased BHB plasma levels well above those seen by BHB salts or MCT oil alone, as evidence of a synergistic effect between the combination of $Na^+/K^+$ BHB salt and MCT oil. By day 3, administration of the combination of MCT and $Na^+/K^+$ BHB salt solution resulted in elevated and sustained BHB plasma levels after the oral supplementation past the 120 minute time point.

TABLE 2

Mean blood βHB levels of a 100 kg male subject over 3 days following a single daily oral administration of either βHB salts (4% solution containing 11 grams sodium βHB and 7.1 grams potassium βHB), MCT oil or βHB salts + MCT oil at 15, 30, 60, 120, 240 and 480 minutes. BHB Salt solution (diluted 4% BHB) MCT (1:1 ratio of C8:C10)

| Hour | 4% BHB salt solution (450 mL) | MCT (30 mL) | 4% BHB salt solution (450 mL) + MCT (30 mL) |
|---|---|---|---|
| 0 | 0.23 | 0.20 | 0.20 |
| 15 | 0.70 | 0.30 | 0.53 |
| 30 | 0.93 | 0.53 | 0.83 |
| 60 | 0.93 | 0.53 | 1.33 |
| 120 | 0.77 | 0.47 | 1.10 |
| 240 | 0.27 | 0.13 | 0.63 |
| 480 | 0.27 | 0.13 | 0.50 |

Example 2—A 70 kg Male Subject

Figure 2:
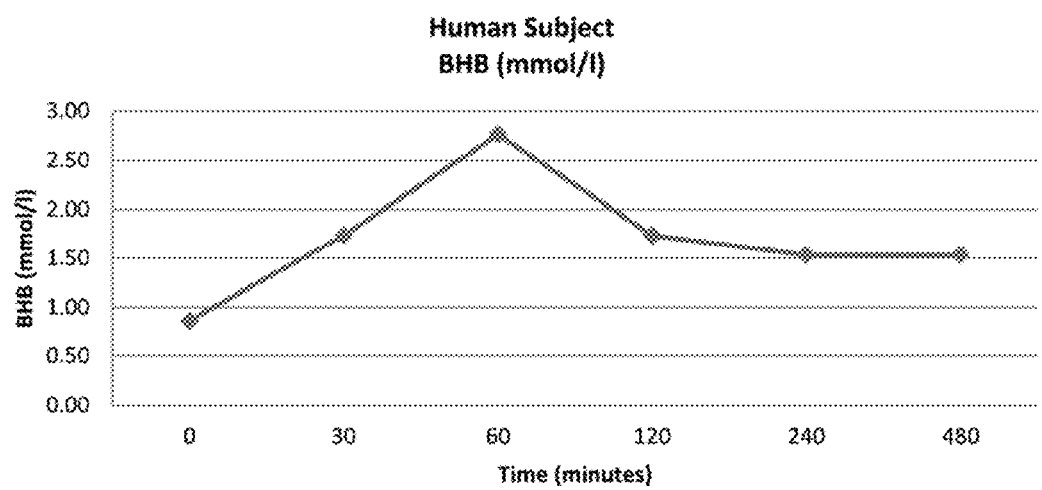
FIG. 2 is a graph depicting mean blood βHB levels after a single administration of βHB salts (4% solution containing 11 grams sodium βHB and 7.1 grams potassium βHB) in a fasted 70 kg male subject on three consecutive days at 30, 60, 120, 240 and 480 minutes after oral administration.

Subject (70 kg male) was instructed to fast for three days, and was given a single daily oral administration of either βHB salts (4% solution containing 11 grams sodium βHB and 7.1 grams potassium βHB), MCT oil or βHB salts+MCT oil at 15, 30, 60, 120, 240 and 480 minutes on 3 consecutive days. At 15, 30, 60, 120, 240 and 480 minutes after administration, blood was drawn. The subject returned on days 2 and 3 for additional supplements, with blood taken as on day 1, as in Example 1. BHB levels were determined as discussed in example 1. Administration of the combination of MCT oil and BHB salts over concurrent days resulted in elevated and sustained BHB levels after oral administration, as seen in FIG. 2. Interestingly, as supplementation progressed to day 2 and day 3, elevated levels of BHB were observed sooner after supplementation and were sustained for a considerably longer time after administration, while peak BHB levels were consistent with Example 1 occurred at 60 minutes after administration, as seen in Table 3.

TABLE 3

Blood βHB levels of a 70 kg male subject following a single daily oral administration of βHB salts (4% solution containing 11 grams sodium βHB and 7.1 grams potassium βHB), at 15, 30, 60, 120, 240 and 480 minutes on 3 consecutive days.

| Time | Day 1 | Day 2 | Day 3 | Mean |
|---|---|---|---|---|
| FASTED + BHB salts (450 mL) | | | | |
| 0 | 0.2 | 0.6 | 1.8 | 0.87 |
| 30 | 0.7 | 1.8 | 2.7 | 1.73 |
| 60 | 1.1 | 2.4 | 4.8 | 2.77 |
| 120 | 0.3 | 1.6 | 3.3 | 1.73 |
| 240 | 0.4 | 1.2 | 3 | 1.53 |
| 480 | 0.6 | 1.6 | 2.4 | 1.53 |

Figure 3:
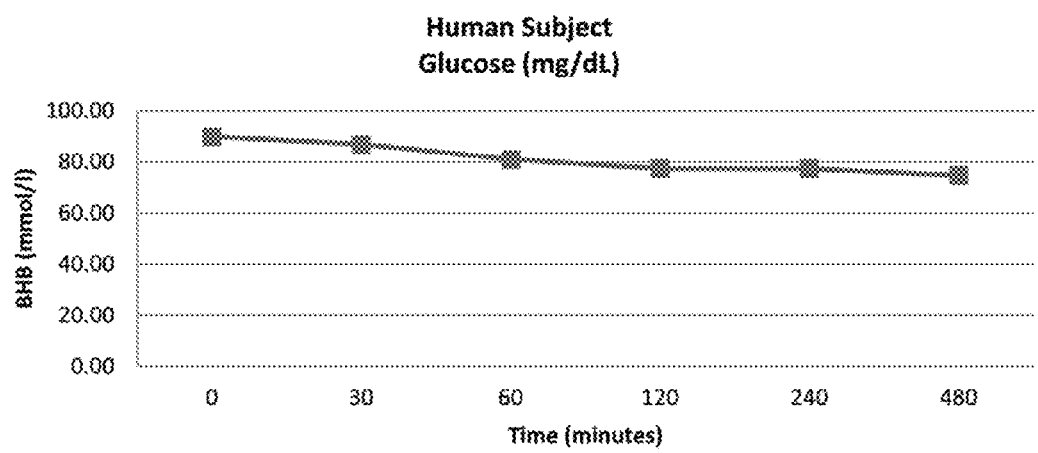
FIG. 3 is an graph depicting mean blood βHB and glucose levels after a single administration of βHB salts (4% solution containing 11 grams sodium βHB and 7.1 grams potassium βHB) in a fasted 70 kg male subject on 3 consecutive days at 30, 60, 120, 240 and 480 minutes after administration.

Blood glucose levels were determined as described above. Supplementation reduced plasma levels of glucose slightly, without any glucose peaks seen through the course of supplementation, as seen in FIG. 3. Supplementation showed reduced glucose throughout the time period analyzed following administration of combination of MCT and BHB salts, with a lower starting glucose level on each subsequent day, as seen in Table 4.

TABLE 4

Blood glucose levels of a 70 kg male subject following a single daily oral administration of βHB salts (4% solution containing 11 grams sodium βHB salt and 7.1 grams potassium βHB salt), or MCT oil or βHB salts + MCT oil at 15, 30, 60, 120, 240 and 480 minutes on 3 consecutive days.

| Time | Day 1 | Day 2 | Day 3 | Mean |
|---|---|---|---|---|
| FASTED + BHB salts (450 mL) | | | | |
| 0 | 100 | 90 | 80 | 90.00 |
| 30 | 95 | 95 | 71 | 87.00 |
| 60 | 85 | 90 | 68 | 81.00 |
| 120 | 82 | 85 | 65 | 77.33 |
| 240 | 80 | 84 | 68 | 77.33 |
| 480 | 76 | 80 | 68 | 74.67 |

Example 3—Fasting Individuals

A combination of MCT and βHB salts, seen in the examples 1 and 2, was orally administered to fasting individuals to accelerate the induction of ketosis and to study the impact of the supplement in short-term severe caloric restriction, short term fasting or intermittent fasting (e.g., alternate day fasting). The supplement provided no more than 400 calories per day and the length of time of the various restrictions and fasts were between 2 and 7 days. Rapid induction of ketosis was associated with improved compliance with caloric restriction and fasting, presumably by reducing hunger and "glucose withdrawal" symptoms (e.g., brain fog).

Caloric restriction and/or fasting resulted in substantial improvements in metabolic biomarkers related to inflammation and insulin resistance, thereby permitting individuals to lose weight and improve general health in a short period of time. Individuals with high blood glucose or type II diabetes may receive particular benefits from this supplement as it has the potential to cause a lasting improvements in insulin sensitivity and overall metabolic health (e.g., improved glucose and lipid profiles). This invention is useful for initiating and sustaining a ketogenic lifestyle by helping a subject get into ketosis quickly. The utilization of the supplement in conjunction with fasting accelerates a subject's ability to induce ketosis and is accompanied by a minimum degree of physical and mental discomfort and a minimal amount of loss of lean body mass.

Example 4—Adult Male Sprague-Dawley Rats

Subject rats (n=74), 275-325 grams, were randomly assigned to a control group (no supplementation) or to one of three ketone precursor groups: medium chain triglyceride (MCT) oil (MO), mineral (Na+/K+) salt of β-hydroxybutyrate (βHB) (SO), or SO+MO 1:1 combination (SM). The ketone mineral salt was developed and synthesized by Dr. Patrick Arnold from Prototype Nutrition. Pure pharmaceutical grade MCT oil was purchased from Now Foods (Bloomingdale, Ill.). SM was mixed at a 1:1 ratio.

Rats were supplemented with medium chain triglyceride (MCT) oil (MO), or a mineral (Na+/K+) salt of β-hydroxybutyrate (βHB) (SO), or SO+MO 1:1 mixture (SM) and force fed a daily at a dose of 5 g/kg body weight on days 1-14, followed by a 10 g/kg dose on days 15-28 rats Supplementation was given between 10 am and 1 pm daily to eliminate variance based on regular eating patterns. Diets were not restricted for this study.

Effects of Ketone Supplementation on Blood Glucose, Ketones, and Lipids:

Once a week, animals were fasted for 4 hours prior to intragastric gavage of the appropriate ketone supplement. The four hour food restriction was used to eliminate normal variance in blood glucose and ketone levels due to food consumption. Whole blood samples (10 µL) were acquired from the saphenous vein of the subjects for analysis of glucose and βHB utilizing the commercially available glucose and ketone monitoring system Precision Xtra™ (Abbott Laboratories, Abbott Park, Ill.) at time intervals of 0, 0.5, 1, 4, 8, and 12 hours after ketone precursor supplements were administered, or until βHB returned to baseline. On Day 0 (Week 0) and Day 28 (Week 4), whole blood samples (10 µL) were acquired for analysis of total cholesterol, HDL, and triglycerides for a lipid panel utilizing the commercially available home cholesterol analyzer Cardio Chek™ (Polymer Technology Systems, Inc., Indianapolis, Ind.) at time 0. Animals were weighed once per week to maintain accurate dosage using the Mittler Toledo SB16001 scales.

Dietary Ketone Supplementation does not Affect Lipid Profile

Figure 4:
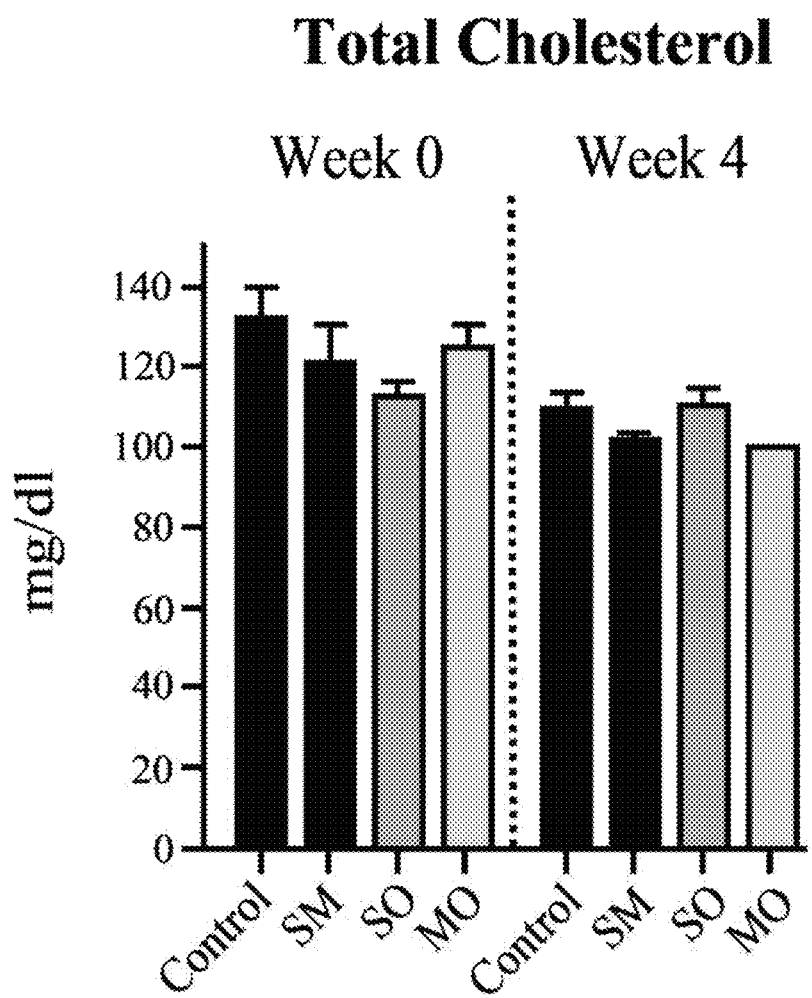
FIG. 4 is a graph showing that ketone supplementation does not affect lipid profile. At week 0 (prior to administration) and week 4 total cholesterol were not significantly different from control in any of the test substances. Statistical analysis was performed using two-way analysis of variance (ANOVA) with Dunnett's post hoc test, results are considered significant if $p<0.05$. Error bars represent ± the standard error of the mean (SEM).
Figure 5:
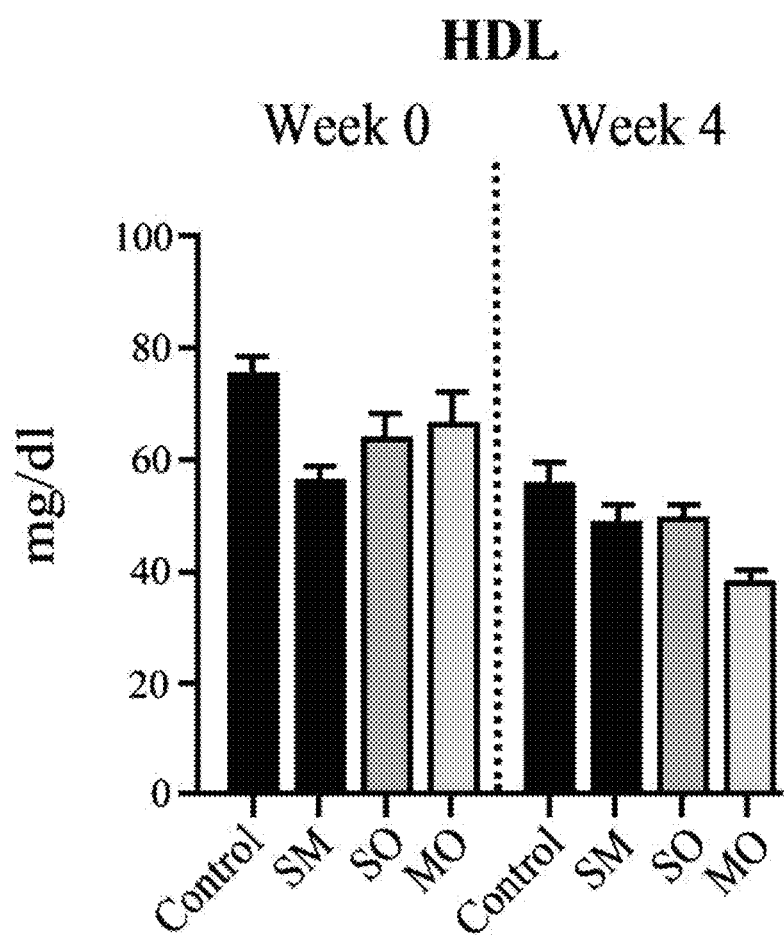
FIG. 5 is a graph showing that ketone supplementation does not affect lipid profile. At week 0 and week 4, HDL levels were not significantly different from the control in any of the treatment groups. Two-way ANOVA with Dunnett's post hoc test results considered significant if $p<0.05$. Error bars represent ±SEM.
Figure 6:
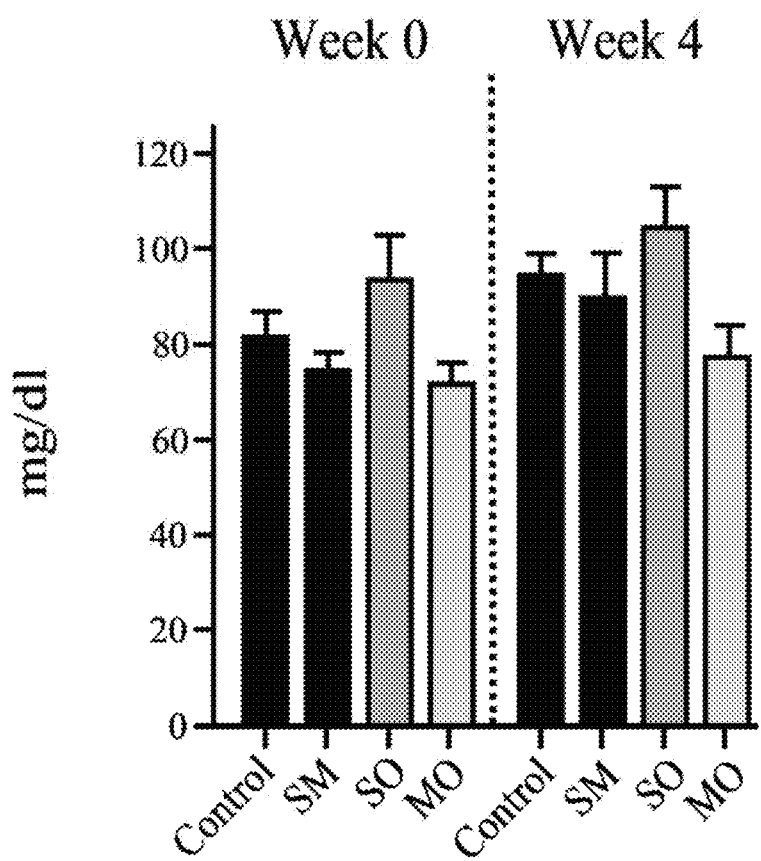
FIG. 6 is a graph showing that ketone supplementation does not affect lipid profile. At week 0 and week 4 triglycerides were not significantly different from control in any of the treatment groups. Two-way ANOVA with Dunnett's post hoc test, results considered significant if $p<0.05$. Error bars represent ±SEM.
Figure 7A:
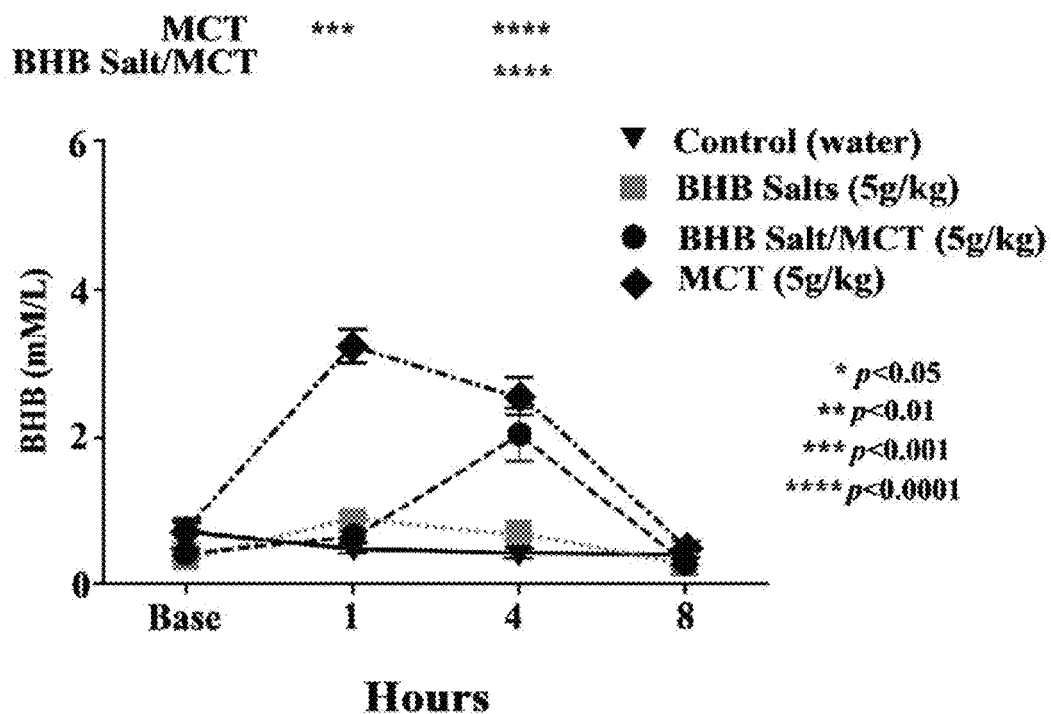
FIGS. 7(A) and (B) are graphs showing the effects of ketone supplementation on blood ketone levels in rats. Ketone supplementation demonstrated significant elevation of blood ketones over 4 weeks. (A) Week 0 and (B) week 1, ketone supplements were given in an oral dosage of 5 g per kg body weight Animals given MCT oil supplementation alone showed significantly elevated blood ketones starting at 30 min and lasting for 8 hours; The combination of βHB salt/MCT oil significantly elevated ketones at 4 hrs. βHB salt alone did not significantly elevate ketones. Two-way ANOVA with Dunnett's post hoc test, results considered significant if $p<0.05$. Error bars represent ±SEM.
Figure 7B:
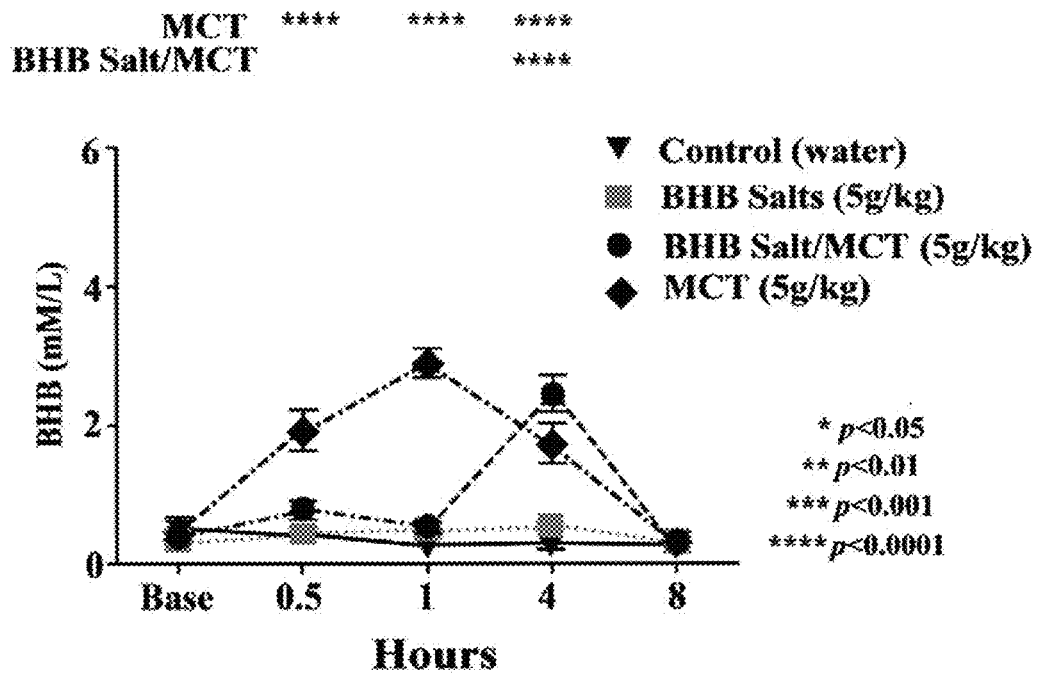

Total Cholesterol and HDL, taken at week 0 and again at week 4, showed a reduction in all samples, including the control, as seen in FIGS. 4 and 5. Analysis showed the levels in all supplements were not significantly different from control after a 4-week chronic dosage of ketone supplements. Triglyceride levels were mildly elevated at week 4 in the control, βHB/MCT sample, or βHB salt sample, with little change in levels of MCT sample, as seen in FIG. 6. However, none of the levels were significantly different from control after a 4-week chronic dosage of ketone supplements.

Ketone Supplementation Causes Rapid and Sustained Elevation of βHB

Figure 8A:
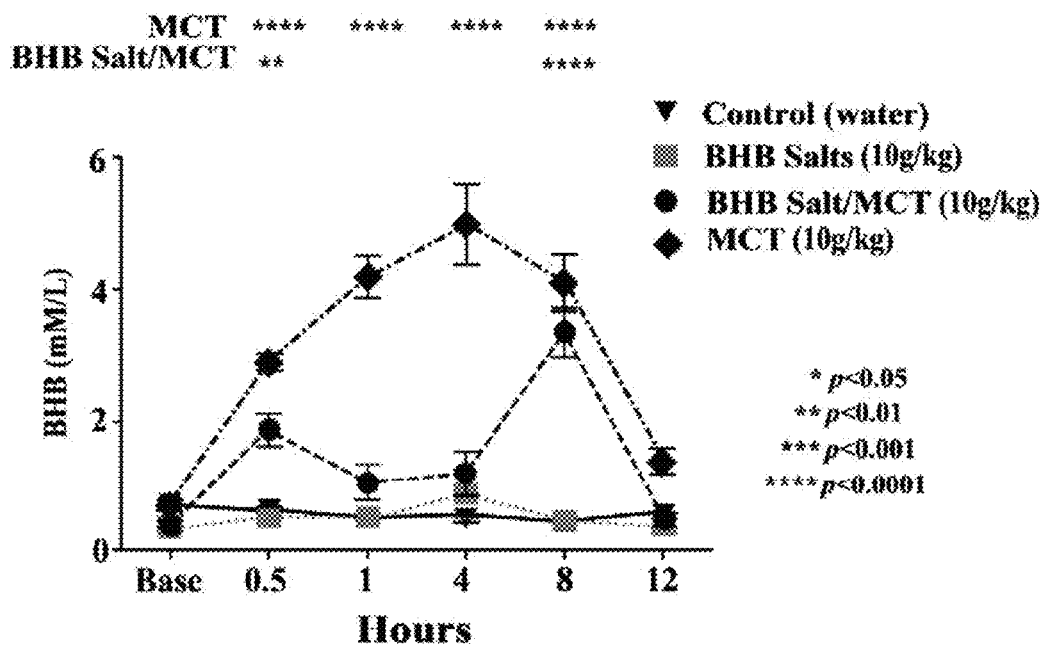
FIGS. 8(A) and (B) are graphs showing the effects of ketone supplementation on blood ketone levels in rats. Ketone supplementation demonstrated significant elevation of ketones over 4 weeks. In week 2 (FIG. 8($a$)) and week 3 (FIG. 8($b$)), the dose of ketone supplements was increased to 10 g/kg for both βHB salt/MCT oil and MCT oil. Blood ketone levels were significantly elevated at 30 minutes, lasting until 12 hours with βHB salt/MCT oil peaking at 8 hours and MCT oil peaking at 4 hours. Supplementation with MCT oil alone resulted in significantly elevated blood ketones starting at 30 minutes and lasting for 8 hours; Treatment with a combination of βHB salt/MCT oil caused significantly elevated blood ketones at 4 hours. βHB salt alone did not significantly elevate ketones. Two-way ANOVA with Dunnett's post hoc test, results considered significant if $p<0.05$. Error bars represent ±SEM.
Figure 8B:
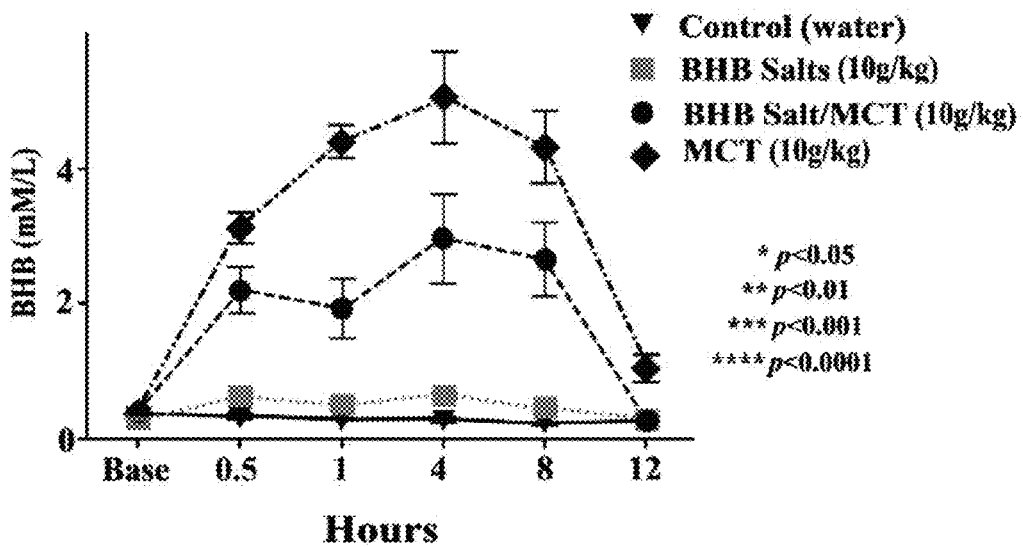
Figure 9:
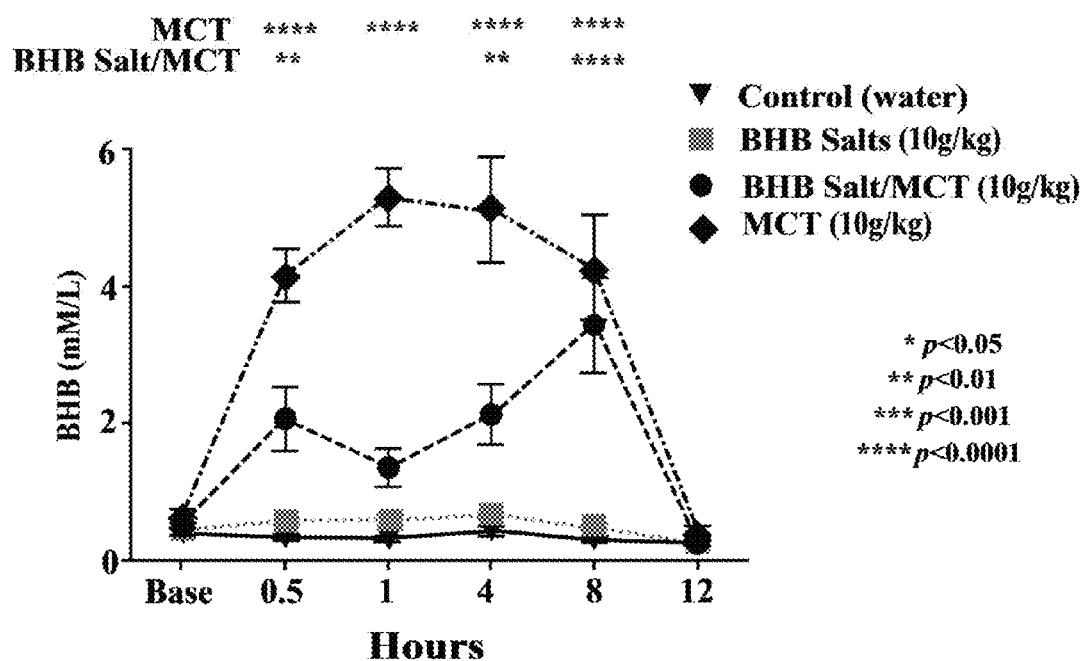
FIG. 9 is a graph showing the effects of ketone supplementation on blood ketone levels in rats. Ketone supplementation demonstrated significant elevation of blood ketones over 4 weeks. In week 4, the dose of ketone supplements was increased to 10 g/kg for both the βHB salt/MCT oil combination treatment group and the MCT oil alone treatment group. Blood ketones were significantly elevated beginning at 30 minutes and lasting for 12 hours, with βHB salt/MCT oil peaking at 8 hours and MCT oil peaking at 4 hours. Ketone supplementation with MCT oil resulted in significantly elevated ketones starting at 30 min and lasting for 8 hours; supplementation with the combination of βHB salt and MCT oil resulted in significantly elevated ketones at 4 hours. Supplementation with βHB salt alone did not significantly elevate ketones. Two-way ANOVA with Dunnett's post hoc test, results considered significant if $p<0.05$. Error bars represent ±SEM.

Over the 28-day experiment, ketone supplements significantly elevated blood ketone levels without dietary restriction, as seen in FIGS. 7(A) through 9. The 5 g/kg dose for days 1-14 showed rapid elevation for the MCT oil at about 30 minutes to one hour with maximum effect at 60 minutes and sustained significant elevation until 8 hours. By weeks 2 and 3, when the dosage of MCT was increased to 10 g/kg, the βHB levels increased to a maximum level at 4 hours, followed by dropping levels of βHB, however BHB levels were still elevated in comparison to the control group, as seen in FIGS. 8(A) and (B). By week 4, the MCT oil began having an earlier effect in elevated BHB levels, with βHB levels further elevated at 30 minutes and levels spiking at 1 hour, as seen in FIG. 9. However, βHB levels at 4 and 8 hours appear to remain at about the same as BHB levels in weeks 2 and 3.

The 1:1 βHB salt/MCT oil combination (SM) at 5 g/kg showed significant elevation after 4 hours, but BHB levels dropped and were no longer significant at 8 hours in weeks 0 and 1. In week 2, SM was administered at 10 g/kg and started to show mild elevation earlier, which was found significant, as seen in FIG. 8(A). Further βHB levels were elevated at 8 hours beyond what was seen in weeks 0 and 1, to levels similar to MO. By week 3, the SM showed elevated βHB levels starting at 30 minutes, though less dramatic than MO, as seen in FIG. 8(B). Further, the βHB levels were elevated at 1 and 4 hours, which was not apparent at weeks 0 through 3, and the βHB levels at 8 hours were slightly depressed. That said, βHB levels were increased to significant levels from 30 minutes to 8 hours after supplementation. By week 4 of SM supplementation, βHB levels were elevated at 8 hours, similar to βHB levels seen with MO supplementation, as seen in FIG. 9.

SO supplementation did not show significant elevation at any time point. With dose escalation to 10 g/kg in groups Control, MO, SO, and SM, for days 14-28, both MO and SM were elevated at 30 min and remained significantly elevated for up to 12 hours, shifting their peak times to MO at 4 hours and SM at 8 hours. SO did not show significant elevation at any time points even with escalated dosage.

Ketone supplementation causes rapid reduction in blood glucose.

Figure 10A:
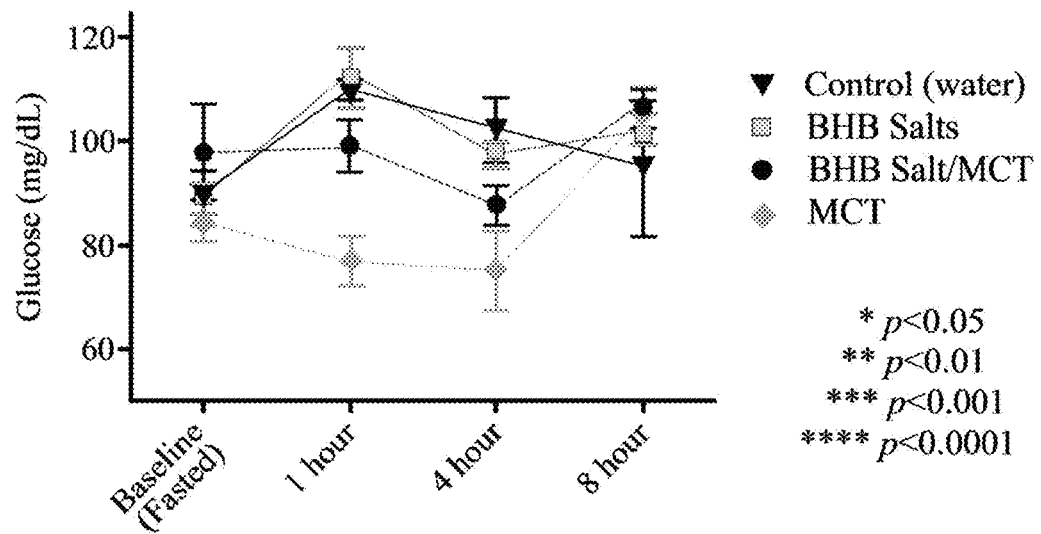
FIGS. 10(A) and (B) are graphs showing the effects of ketone supplementation in rats on blood glucose levels at (A) week 0 and (B) week 1. Two-way ANOVA with Dunnett's post hoc test, results considered significant if $p<0.05$. Error bars represent ±SEM.
Figure 10B:
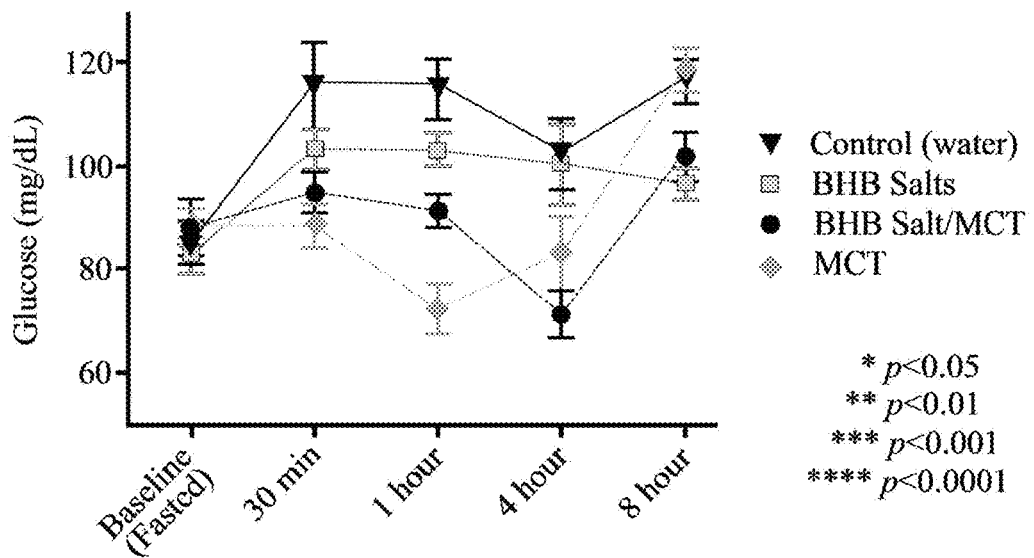
Figure 11A:
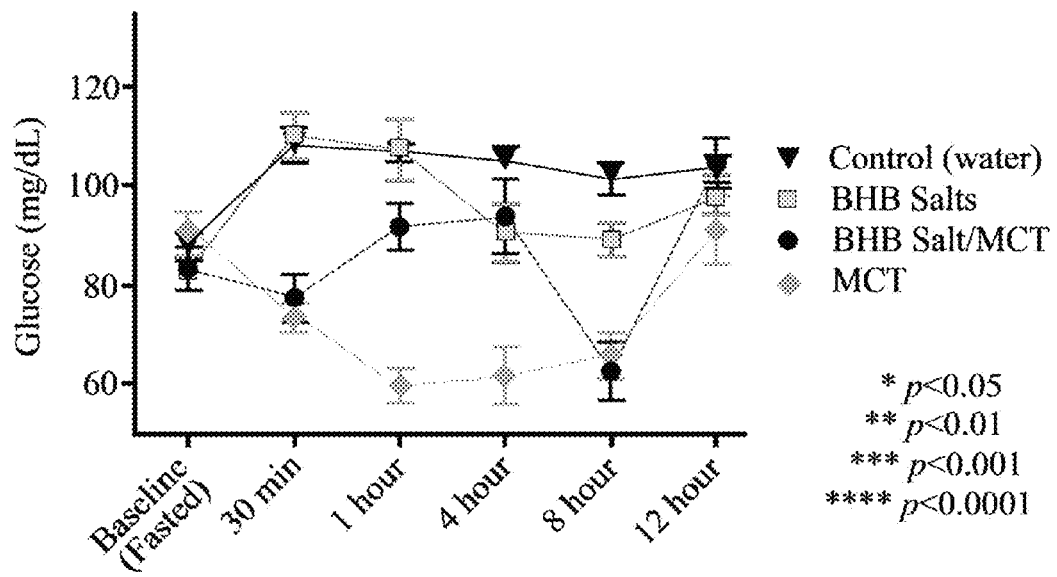
FIGS. 11(A) and (B) are graphs showing the effects of ketone supplementation in rats on blood glucose levels at (A) week 2 and (B) week 3. Two-way ANOVA with Dunnett's post hoc test, results considered significant if $p<0.05$. Error bars represent ±SEM.
Figure 11B:
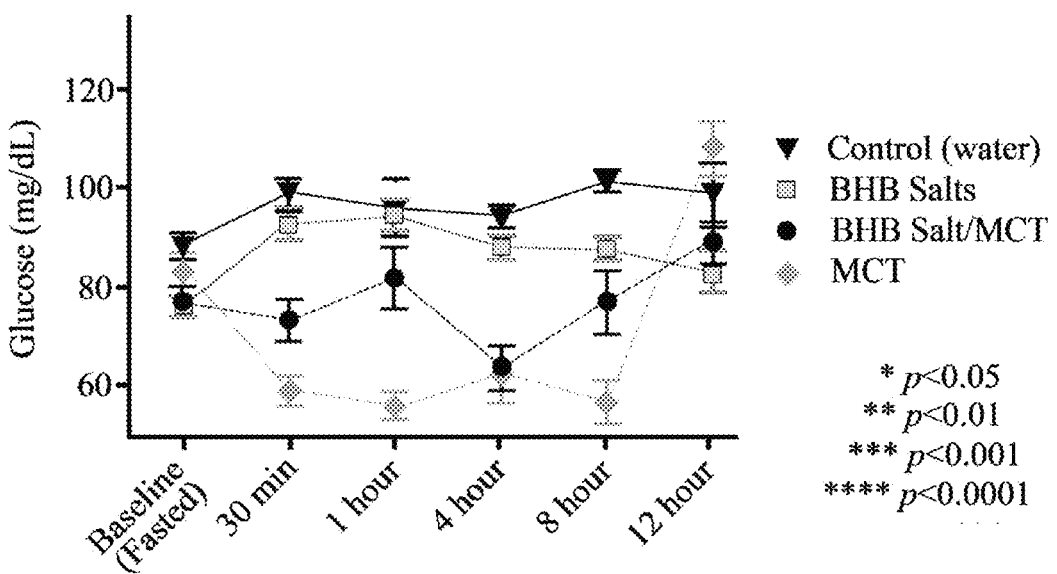
Figure 12:
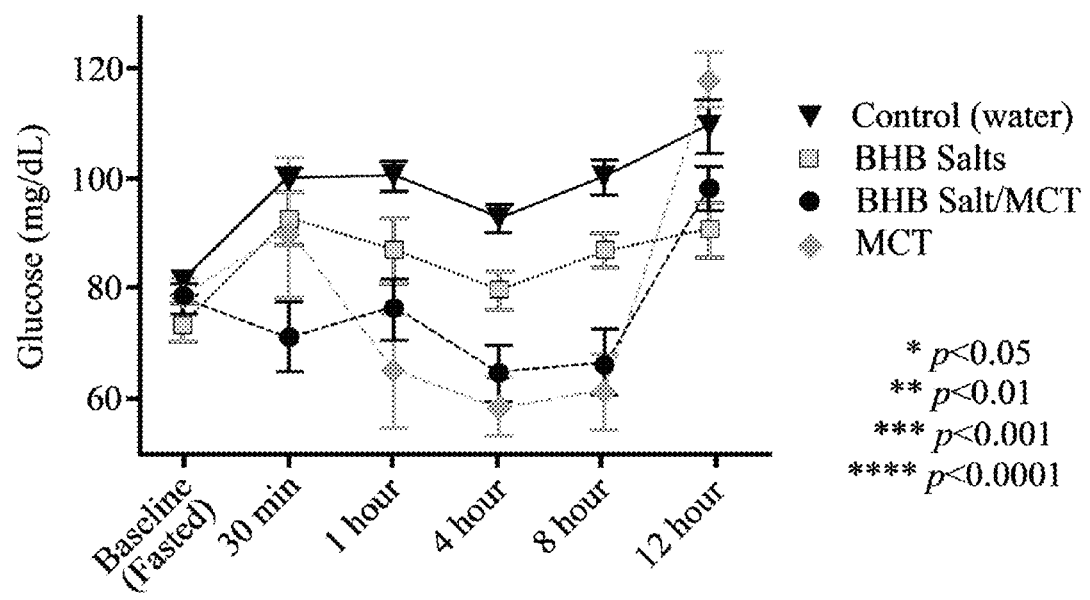
FIG. 12 is a graph showing the effects of ketone supplementation in rats on blood glucose levels at week 4. Two-way ANOVA with Dunnett's post hoc test, results considered significant if $p<0.05$. Error bars represent ±SEM.

SO supplementation did not show any significant difference compared to control at week 0, whereas MO and SM reduced glucose through 4 hours after supplementation, seen in FIGS. 10(A) and (B). However, SO began reducing glucose by 8 hours at week 1. By week 2 onward, with an increase in supplementation dosage to 10 g/kg, SO, MO and SM had reduced glucose levels at 30 minutes through 8 hours, with normalization to about control levels by 12 hours, as seen in FIGS. 11 through 12.

The Effects of Ketone Supplementation on Organ Weight:

At the end of 4 weeks, rats were force fed at time 0 then sacrificed by $CO_2$ between 4-8 hours, which were determined to be peak BHB level elevation. Brain, lungs, liver, kidneys, spleen and heart were harvest and weighed using AWS-1000 1 kg portable digital scale (AWS, Charleston, S.C.). Organs were then either flash frozen in liquid nitrogen or preserved in paraformaldehyde for future analysis.

Figure 13A:
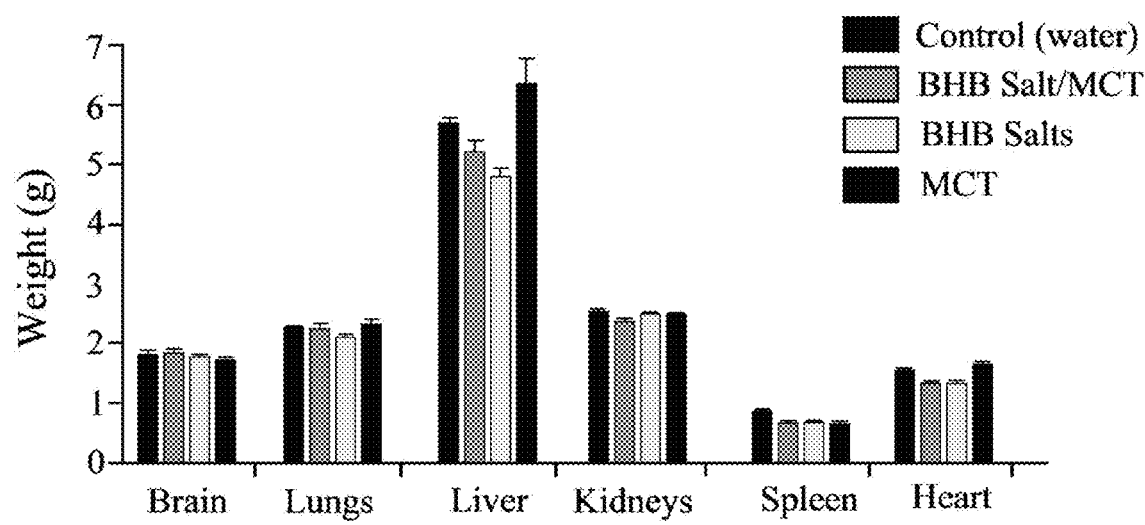
FIGS. 13(A) and (B) are graphs showing the effects of ketone supplementation in rats on (A) organ weights, and (B) liver weights. At week 4, harvested liver weights were significantly decreased in rats fed a combination of βHB Salt and MCT oil and those fed only βHB salt, whereas liver weights were significantly increased in animals supplemented with only MCT oil. Two-way ANOVA with Dunnett's post hoc test, results considered significant if $p<0.05$. Error bars represent ±SEM.
Figure 13B:
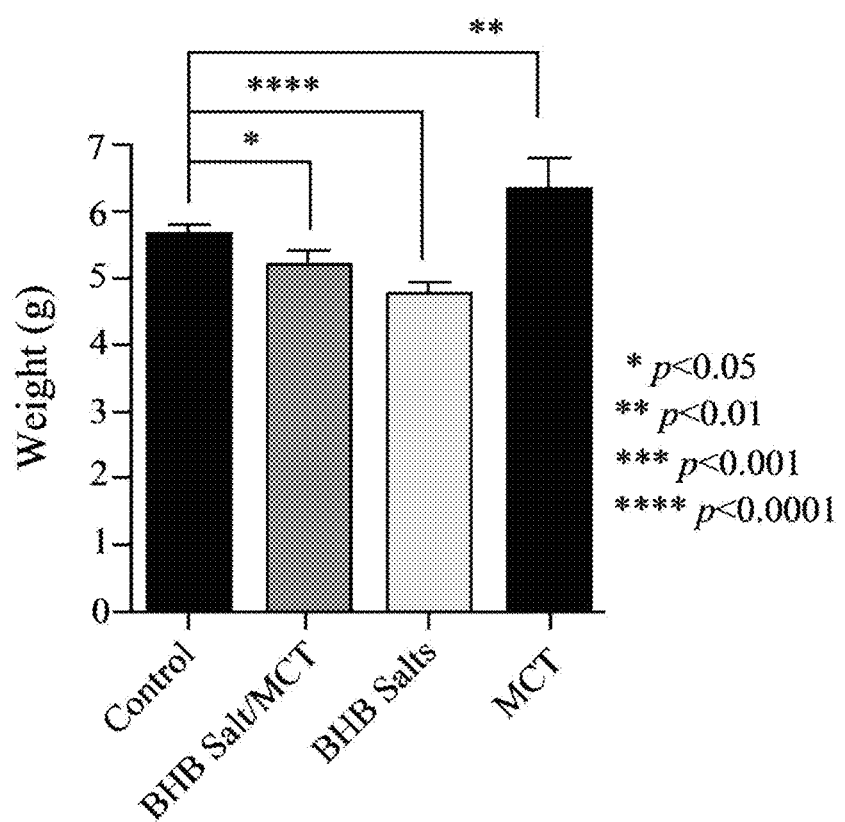

At the end of 4 weeks, livers were harvested and weighed per subject rats. SO and SM ketone supplements significantly decreased the weight of the liver. MO significantly increased the weight of livers in the subjects, as seen in FIG. 13(B). No other organ showed significant differences in weight across the three ketone precursors, as seen in FIG. 13(A).

Ketone Supplementation Effects on Body Weight

Figure 14:
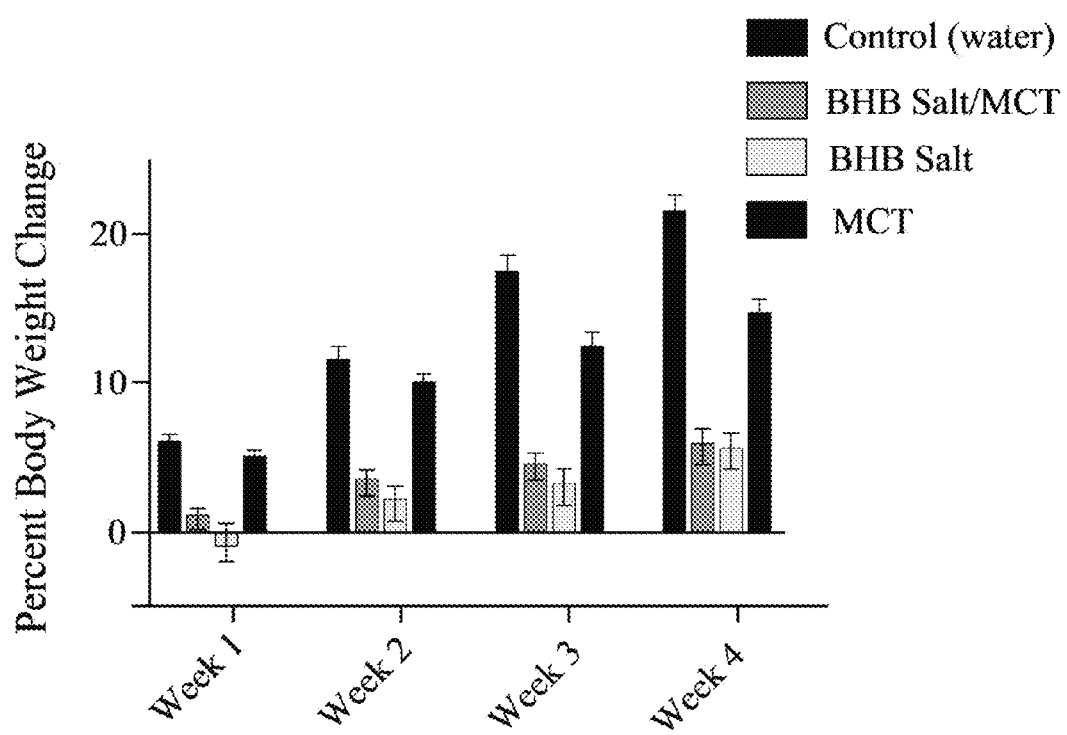
FIG. 14 is a graph showing the effects of ketone supplementation in rats on change of body weight.

Rats were administered SO, MO, or SM daily for 28 days as described above. Each week the animals were weighed. Rats that were treated with SO, MO, or SM gained significantly less weight compared to controls, as seen in FIG. 14. The control animals continued to gain weight throughout the month long study. In comparison, the ketone supplement treatment groups all gained less weight. A 2 to 3 fold reduction in weight gain was noted in the SO and SM groups. A key finding of this study is that the SM group was able to limit weight gain in an unexpected way as the amounts of BHB and MCT when combined were much lower than the amounts of those ingredients used in the SO and MO treatment groups. This effect on body weight gain is likely due to appetite suppression caused by the supplements, rather than a reduced intake of the supplement itself, as force feeding controlled for dosing.

Example 5

In a non-limiting example, a 16-ounce drink formula containing the following ingredients is consumed by an individual three times a day.

TABLE 6

List of ingredients used in preparing a ketosis inducing drink formula.

| Ingredient | Amount |
| --- | --- |
| Sodium beta-hydroxybutyrate | 11 grams (1.9 grams sodium, 9.1 grams beta-hydroxybutyrate) |
| Potassium beta-hydroxybutyrate | 7.1 grams (1.9 grams potassium, 5.2 grams beta-hydroxybutyrate) |
| MCT oil, USP | 30 grams |
| Ancillary Ingredients (not used in tests below) | |
| Calcium beta-methyl-beta-hydroxybutyrate | 1000 milligrams |
| Arginine alpha-ketoglutarate | 1000 milligrams |
| Sodium R-alpha lipoic acid | 100 milligrams |
| Thiamine | 20 mg |
| Riboflavin | 20 mg |
| Niacin | 20 mg |
| Pyridoxine | 20 mg |
| Ascorbic acid | 750 mg |
| Citric acid | 1000 mg |
| Malic acid | 1000 mg |
| Sodium benzoate | 300 mg |
| Potassium sorbate | 300 mg |
| Acesulfame K | 10 mg |
| Aspartame | 30 mg |
| Xanthan gum | 1000 mg |
| Flavoring | — |

The data presented herein supports the use of a unique combination of beta hydroxybutyrate and medium chain triglycerides in order to generate a unique blood ketone profile necessary for effectively entering therapeutic ketosis. There are at least two populations that would immediately benefit from this combination formulation. First, children with epilepsy benefit from ketosis as it has been shown to reduce seizures. Second, people that are looking to lose weight, suppress the appetite, and enhance physical performance benefit from ketosis to enhance their results. In both populations, adherence to a ketogenic, carbohydrate-restricted diet as a means of generating ketosis is limited by the difficulty of generating blood ketone levels that are sufficiently elevated and prolonged. Slow entry into ketosis leads to prolonged side effects such as physical distress and mood depression. Additionally, even slight deviations from the ketogenic diet cause pertubations in blood ketone levels, thereby quickly kicking the subject out of therapeutic ketosis. The data presented herein show that the combination of BHB and MCT results in a more rapid induction of ketosis, with greater peak levels of blood ketones, and longer sustainment of ketosis, compared to either component alone, thereby overcoming the drawbacks of current approaches.

The combination of BHB and MCT is unique in that it also avoids the complications that arise from using either substance alone. Consuming sufficient amounts of BHB salts in order to quickly enter and maintain ketosis results in sodium overload and electrolyte imbalances and therefore is not practical. Consuming sufficient quantities of MCT in order to quickly enter and maintain ketosis results in severe gastrointestinal distress and therefore is also not practical. The data presented herein shows that reduced amounts of both substances can be used in combination, and not only improves tolerability, but also generates a unique blood ketone profile that has benefits not seen with the individual components when used in isolation.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

It is also to be understood that the following claims are intended to cover all of the generic and specific features of the invention herein described, and all statements of the scope of the invention which, as a matter of language, might be said to fall therebetween.

What is claimed is:

1. A method of promoting or sustaining ketosis in a mammal, comprising:
   administering at least one medium chain fatty acid or ester thereof in an amount between about 5 grams and about 50 grams per day for at least one day; and
   administering at least one beta-hydroxybutyrate compound, where the at least one beta-hydroxybutyrate compound is beta-hydroxybutyrate monomer salt in an amount between about 2 grams and about 50 grams per day for at least one day.

2. The method of claim 1, wherein the at least one beta-hydroxybutyrate compound comprises one or more of a beta-hydroxy butyrate sodium salt, beta-hydroxy butyrate potassium salt, beta-hydroxy butyrate calcium salt, beta-hydroxy butyrate magnesium salt, sodium beta-hydroxybutyrate, arginine beta-hydroxybutyrate, beta-hydroxy butyrate sodium salt and beta-hydroxy butyrate potassium salt, lysine beta-hydroxybutyrate, histidine beta-hydroxybutyrate, ornithine beta-hydroxybutyrate, creatine beta-hydroxybutyrate, agmatine beta-hydroxybutyrate, citrulline beta-hydroxybutyrate, and combinations thereof.

3. The method of claim 1, wherein the at least one medium chain fatty acid or ester thereof is selected from the group consisting of medium chain triglycerides, coconut oil, coconut milk powder, fractionated coconut oil, palm kernel oil, isolated hexanoic acid, isolated octanoic acid, isolated decanoic acid, ethoxylated triglyceride, enone triglyceride derivatives thereof, aldehyde triglyceride derivatives thereof, monoglyceride derivatives thereof, diglyceride derivatives thereof, triglyceride derivatives thereof, and an alkyl ester thereof.

4. The method of claim 1, wherein the composition further comprises at least one additional component selected from the group consisting of amino acids, amino acid metabolites, vitamins, minerals, coconut milk powder, electrolytes, NADH, tetrahydrobiopeterin, alpha-ketoglutaric acid, alpha lipoic acid, nutritional co-factors, calcium beta-methyl-beta-hydroxybutyrate, arginine alpha-ketoglutarate, sodium R-alpha lipoic acid, thiamine, riboflavin, niacin, pyridoxine, ascorbic acid, citric acid, malic acid, sodium benzoate, potassium sorbate, acesulfame K, aspartame, xanthan gum, and combinations thereof.

5. The method of claim 1, wherein the at least one beta-hydroxybutyrate compound is sodium salt of β-hydroxybutyrate and potassium salt of β-hydroxybutyrate, and
   wherein the at least one medium chain fatty acid and beta-hydroxybutyrate salt mixture is at a ratio of 1:1 β-hydroxybutyrate salt to medium chain fatty acid.

6. The method of claim 1, wherein the composition is administered once per day, twice per day, or three times per day to a patient in need thereof.

7. The method of claim 1, wherein the mammal is a human.

8. The method of claim 1, wherein the at least one beta-hydroxy compound comprises:
   sodium beta-hydroxybutyrate, arginine beta-hydroxybutyrate, or a combination thereof; or
   a combination of beta-hydroxy butyrate sodium salt and beta-hydroxy butyrate potassium salt.

9. The method of claim 1, wherein the at least one beta-hydroxy butyrate compound comprises racemic DL-beta hydroxybutyrate or the single isomer R-beta hydroxybutyrate.

10. The method of claim 1, wherein about 5 grams to about 30 grams of the at least one beta-hydroxybutyrate compound is administered per day.

11. The method of claim 1, further comprising administering to the mammal at least one non-toxic mineral salt.

12. The method of claim 1, wherein the at least one medium chain fatty acid or ester thereof and the at least one beta-hydroxybutyrate compound are administered for at least 7 days, or at least 14 days.

13. A method of suppressing appetite or promoting weight loss in a mammal, comprising:
   administering at least one medium chain fatty acid or ester thereof in an amount between about 5 grams and about 50 grams per day for at least one day; and
   administering at least one beta-hydroxybutyrate compound in an amount between about 2 grams and about 50 grams per day for at least one day, where the at least one beta-hydroxybutyrate compound is comprised of a beta-hydroxybutyrate monomer salt.

14. The method of claim 13, wherein the mammal is a human.

15. The method of claim 13, wherein the at least one beta-hydroxybutyrate compound is selected from the group consisting of a beta-hydroxy butyrate sodium salt, beta-hydroxy butyrate potassium salt, beta-hydroxy butyrate calcium salt, beta-hydroxy butyrate magnesium salt, sodium beta-hydroxybutyrate, arginine beta-hydroxybutyrate, beta-hydroxy butyrate sodium salt and beta-hydroxy butyrate potassium salt, lysine beta-hydroxybutyrate, histidine beta-hydroxybutyrate, ornithine beta-hydroxybutyrate, creatine beta-hydroxybutyrate, agmatine beta-hydroxybutyrate, citrulline beta-hydroxybutyrate, and combinations thereof.

16. The method of claim 13, wherein the at least one medium chain fatty acid or ester thereof is comprised of coconut oil, coconut milk powder, fractionated coconut oil, isolated hexanoic acid, isolated octanoic acid, isolated decanoic acid, ethoxylated triglyceride, enone triglyceride derivatives thereof, aldehyde triglyceride derivatives thereof, monoglyceride derivatives thereof, diglyceride derivatives thereof, triglyceride derivatives thereof, and an alkyl ester thereof.

17. The method of claim 13, wherein the composition further comprises at least one additional component selected from the group consisting of amino acids, amino acid metabolites, vitamins, minerals, coconut milk powder, electrolytes, NADH, tetrahydrobiopeterin, alpha-ketoglutaric acid, alpha lipoic acid, nutritional co-factors, calcium beta-methyl-beta-hydroxybutyrate, arginine alpha-ketoglutarate, sodium R-alpha lipoic acid, thiamine, riboflavin, niacin, pyridoxine, ascorbic acid, citric acid, malic acid, sodium benzoate, potassium sorbate, acesulfame K, aspartame, xanthan gum, and combinations thereof.

18. The method of claim 13, wherein the at least one beta-hydroxybutyrate compound is sodium salt of β-hydroxybutyrate and potassium salt of β-hydroxybutyrate, and wherein the at least one medium chain fatty acid and beta-hydroxybutyrate salt mixture is at a ratio of 1:1 β-hydroxybutyrate salt to medium chain fatty acid.

19. The method of claim 13, wherein the at least one medium chain fatty acid or ester thereof and the at least one beta-hydroxybutyrate compound are administered at least once a day for between one and two weeks.

20. The method of claim 13, wherein the composition is administered once per day, twice per day, or three times per day to a patient in need thereof.

21. The method of claim 13, wherein the method further comprises restricting intake of carbohydrates and protein.

22. A method for inducing ketosis in a mammal, comprising:
administering at least one medium chain fatty acid or ester thereof in an amount between about 5 grams and about 50 grams per day for at least one day; and
administering at least one beta-hydroxybutyrate compound in an amount between about 2 grams and about 50 grams per day for at least one day, wherein the at least one beta-hydroxybutyrate compound is comprised of a beta-hydroxybutyrate monomer salt,
wherein the at least one medium chain fatty acid or ester thereof and the at least one beta-hydroxybutyrate compound are administered in an effective amount so as to induce ketosis for at least 240 minutes.

23. The method of claim 22, wherein the at least one beta-hydroxybutyrate compound is administered in an amount of between about 5 grams and about 30 grams per day for at least one day.

24. The method of claim 22, wherein the at least one beta-hydroxybutyrate compound is administered in an amount of between about 10 grams and about 20 grams per day for at least one day.

25. The method of claim 22, wherein the at least one medium chain fatty acid or ester thereof is administered in an amount of between about 10 grams and about 40 grams per day for at least one day.

26. The method of claim 22, wherein the at least one medium chain fatty acid or ester thereof is administered in an amount of between about 15 grams and about 30 grams per day for at least one day.

* * * * *